(12) United States Patent
Wheeler et al.

(10) Patent No.: US 8,367,370 B2
(45) Date of Patent: Feb. 5, 2013

(54) DROPLET-BASED CELL CULTURE AND CELL ASSAYS USING DIGITAL MICROFLUIDICS

(76) Inventors: Aaron R. Wheeler, Toronto (CA); Irena Barbulovic-Nad, Toronto (CA)

( * ) Notice: Subject to any disclaimer, the term of this patent is extended or adjusted under 35 U.S.C. 154(b) by 963 days.

(21) Appl. No.: 12/285,020

(22) Filed: Sep. 26, 2008

(65) Prior Publication Data

US 2009/0203063 A1 Aug. 13, 2009

Related U.S. Application Data

(60) Provisional application No. 61/064,002, filed on Feb. 11, 2008.

(51) Int. Cl.
*C12Q 1/02* (2006.01)
*C12N 5/02* (2006.01)
(52) U.S. Cl. .......................... 435/29; 435/395
(58) Field of Classification Search .................. 435/29, 435/395
See application file for complete search history.

(56) References Cited

U.S. PATENT DOCUMENTS

| | | | |
|---|---|---|---|
| 4,569,575 A | 2/1986 | Le Pesant et al. | |
| 4,636,785 A | 1/1987 | Le Pesant | |
| 4,818,052 A | 4/1989 | Le Pesant et al. | |
| 5,486,337 A | 1/1996 | Ohkawa | |
| 6,352,838 B1 | 3/2002 | Krulevitch et al. | |
| 6,565,727 B1 | 5/2003 | Shenderov | |
| 6,773,566 B2 | 8/2004 | Shenderov | |
| 6,911,132 B2 | 6/2005 | Pamula et al. | |
| 6,989,234 B2 | 1/2006 | Kolar et al. | |
| 7,147,763 B2 | 12/2006 | Elrod et al. | |
| 7,163,612 B2 | 1/2007 | Sterling et al. | |
| 7,214,302 B1 | 5/2007 | Reihs et al. | |
| 7,255,780 B2 | 8/2007 | Shenderov | |
| 7,328,979 B2 | 2/2008 | Decre et al. | |
| 7,329,545 B2 | 2/2008 | Pamula et al. | |
| 2002/0043463 A1 | 4/2002 | Shenderov | |
| 2002/0150683 A1 | 10/2002 | Troian et al. | |
| 2004/0055536 A1 | 3/2004 | Kolar et al. | |

(Continued)

FOREIGN PATENT DOCUMENTS

| WO | 2007120241 A2 | 10/2007 |
|---|---|---|
| WO | WO 2007/120241 A2 | 10/2007 |

(Continued)

OTHER PUBLICATIONS

Swinbanks, D. 1995. Government backs proteome proposal. Nature, vol. 378, No. 6558, p. 653.*

(Continued)

*Primary Examiner* — David Naff
*Assistant Examiner* — Kailash C Srivastava
(74) *Attorney, Agent, or Firm* — Lynn C. Schumacher; Stephen W. Leonard; Hill & Schumacher

(57) ABSTRACT

We introduce a method for implementing cell-based assays and long-term cell culture. The method is based on digital microfluidics (DMF) which is used to actuate nanoliter droplets of reagents and cells on a planar array of electrodes. DMF method is sutable for assaying and culturing both cells in suspension and cells grown on surface (adherent cells). This method is advantageous for cell culture and assays due to the automated manipulation of multiple reagents in addition to reduced reagent use and analysis time. No adverse effects of actuation by DMF were observed in assays for cell viability, proliferation, and biochemistry. These results suggest that DMF has great potential as a simple yet versatile analytical tool for implementing cell-based assays and cell culture on the microscale.

55 Claims, 26 Drawing Sheets

U.S. PATENT DOCUMENTS

| | | | |
|---|---|---|---|
| 2004/0058450 | A1 | 3/2004 | Pamula et al. |
| 2004/0171169 | A1 | 9/2004 | Kallury et al. |
| 2004/0211659 | A1 | 10/2004 | Velev |
| 2005/0115836 | A1 | 6/2005 | Reihs |
| 2005/0148091 | A1 | 7/2005 | Kitaguchi et al. |
| 2005/0191759 | A1 | 9/2005 | Pedersen-Bjergaard et al. |
| 2007/0023292 | A1 | 2/2007 | Kim et al. |
| 2007/0148763 | A1 | 6/2007 | Huh et al. |
| 2007/0242111 | A1 | 10/2007 | Pamula et al. |
| 2008/0044914 | A1 | 2/2008 | Pamula et al. |
| 2008/0156983 | A1 | 7/2008 | Fourrier et al. |
| 2008/0185339 | A1 | 8/2008 | Delapierre et al. |
| 2008/0281471 | A1 | 11/2008 | Smith et al. |

FOREIGN PATENT DOCUMENTS

| | | | |
|---|---|---|---|
| WO | 2007136386 | | 11/2007 |
| WO | 2008051910 | A3 | 5/2008 |

OTHER PUBLICATIONS

Zergioti et al. 2005. Femtosecond laser microprinting of biomaterials. Applied Physics Letters, vol. 86, pp. 163902-1 to 163902-3.*

Link et al., "Electric Control of Droplets in Microfluidic Devices", Angew. Chem. Int. Ed. 2006, 45, pp. 2556-2560.

Moon et al., "An integrated digital microfluidic chip for multiplexed proteomic sample preparation and analysis by MALDI-MS", Lab Chip. Sep. 2006/ vol. 6(9), 1213-1219.

Wheeler et al, "Electrowetting-based microfluidics for analysis of peptides and proteins by matrix=assisted laser desorption/ionization mass spectrometry" Anal Chem., Aug. 15, 2004, vol. 76 (16), 4833-4838.

Chatterjee et al., "Droplet-based microfluidics with nonaqueous solvents and solutions", Lab Chip, Feb. 2006, vol. 6(2), 199-206.

Marc A. Unger. "Monolithic Microfabricated Valves and Pumps by Multilayer Soft Lithography," SCIENCE (2000) vol. 288.

Hongmei Yu. "A plate reader-compatible microchannel array for cell biology assays," The Royal Society of Chemistry (2007) Lab Chip vol. 7, pp. 388-391.

A.S. Verkman, "Drug Discovery In Academia," Am J Physiol Cell Physiol (2004) vol. 286, pp. 465-474.

Jamil El-Ali. "Cells on chips," NATURE (2006) Insight Review, vol. 442.

Eun Zoo Lee, "Removal of bovince serum albumin using solid-phase extraction with in-situ polymerized stationary phase in a microfluidic device," ScienceDirect , Journal of Chromatography A. (2008) vol. 1187 pp. 11-17.

Shih-Kang Fan. "Cross-scale electric manipulations of cells and droplets by frequency-modulated dielectrophoresis and electrowetting" The Royal Society of Chemistry (2008), Lab Chip vol. 8, pp. 1325-1331.

Ting-Hsuan Chen. "Selective Wettability Assisted Nanoliter Sample Generation Via Electrowetting-Based Transportation," Proceedings of the Fifth International Conference on Nanochannels, Microchannels and Minichannels (ICNMM) (Jun. 18-20, 2007).

Hsih Yin Tan, "A lab-on-a-chip for detection of nerve agent sarin in blood," The Royal Society of Chemistry (2008), Lab Chip vol. 8, pp. 885-891.

Mohamed Abdelgawad. "Low-cost, rapid-prototyping of digital microfluidics devices," Springer, Microfluid Nanofluid (2008) vol. 4, pp. 349-355.

Mais J. Jebrail, "Digital Microfluidic Method for Protein Extraction by Precipitation," Anal. Chem. (2009) vol. 81, No. 1.

Eric Lebrasseur. "Two-dimensional electrostatic actuation of droplets using a single electrode panel and development of disposable plastic film card," ScienceDirect, Sensors and Actuators (2007) vol. 136, pp. 358-366.

Kai-Cheng Chuang. "Direct Handwriting Manipulation of Droplets By Self-Aligned Mirror-EWOD Across A Dielectric Sheet," MEMS (Jan. 2006) pp. 22-26.

* cited by examiner

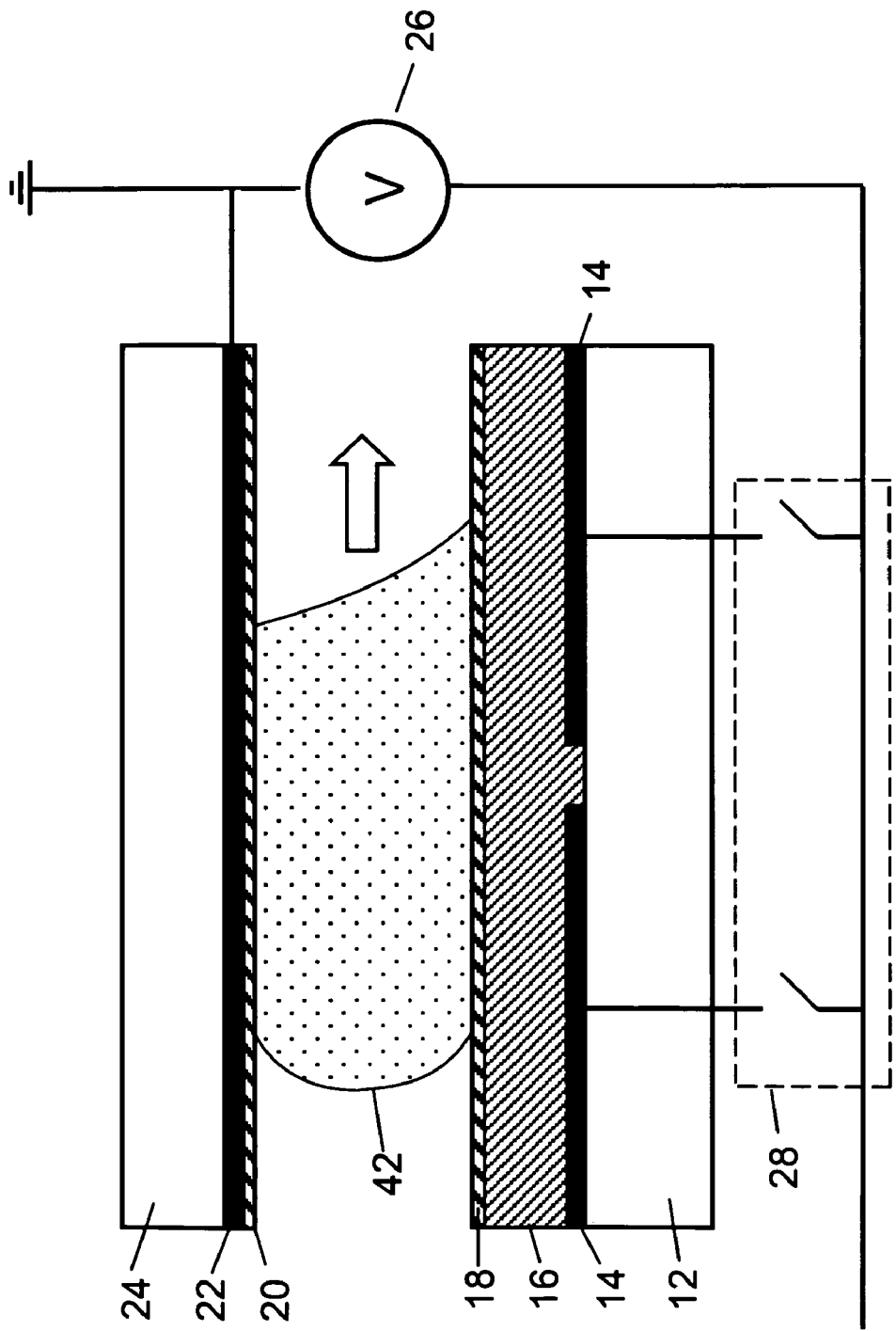

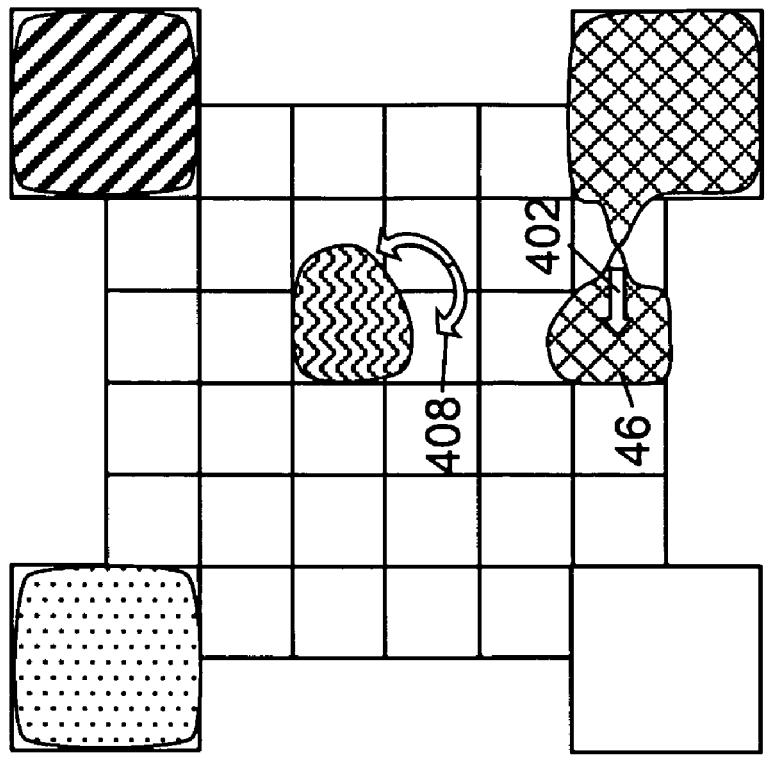
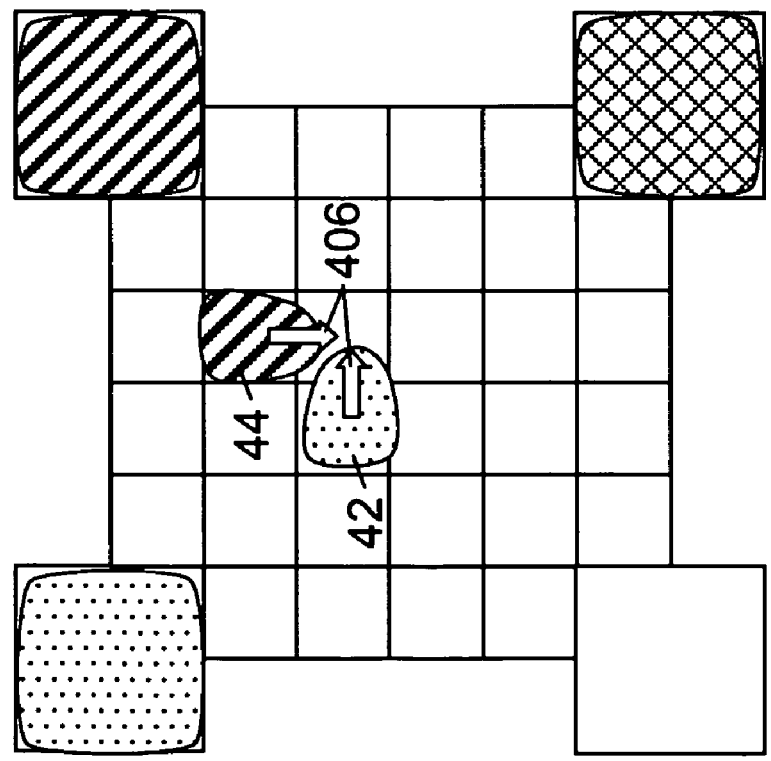
Figure 7(d)
Figure 7(c)

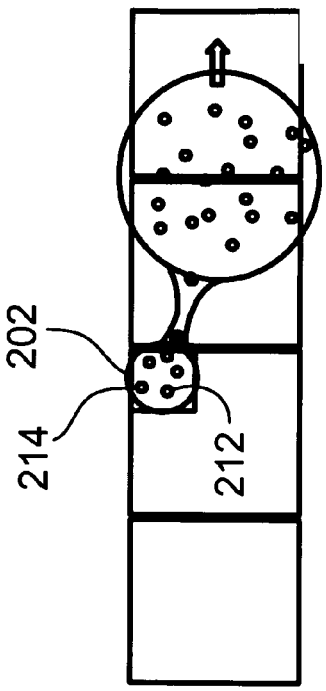
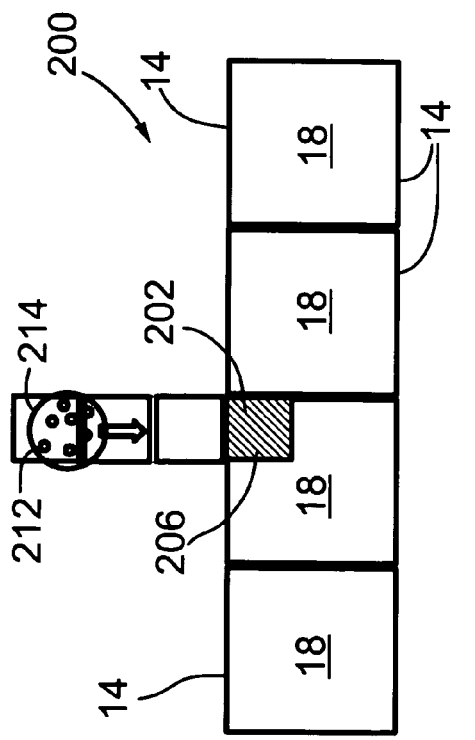
Figure 11 (a)
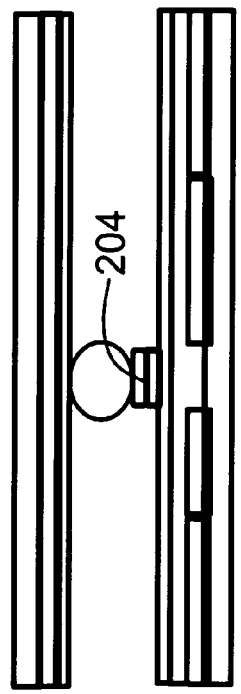
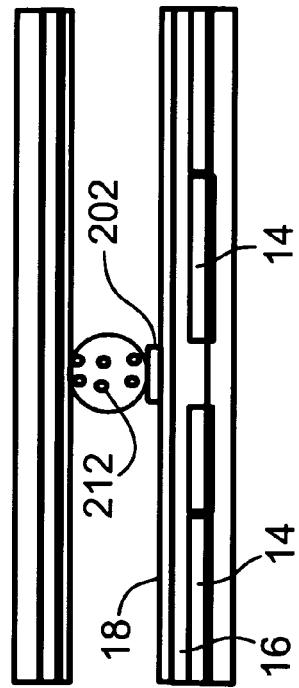
Figure 11 (b)
Figure 11 (c)
Figure 11 (d)

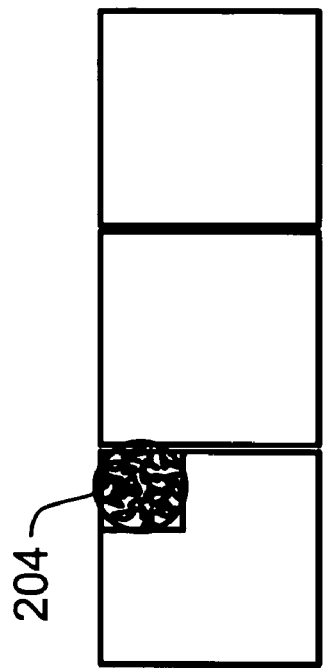
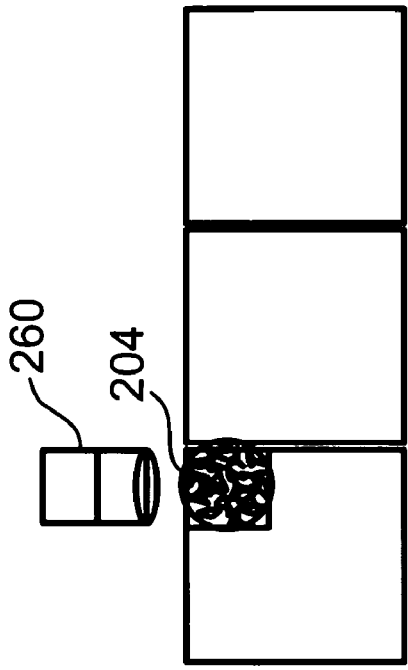
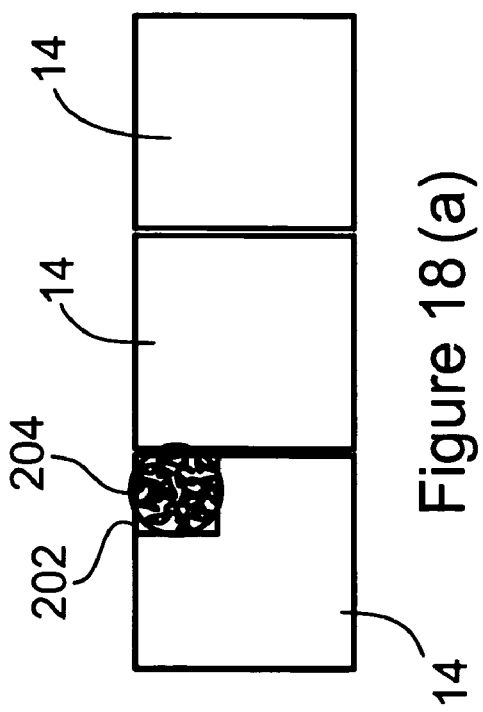
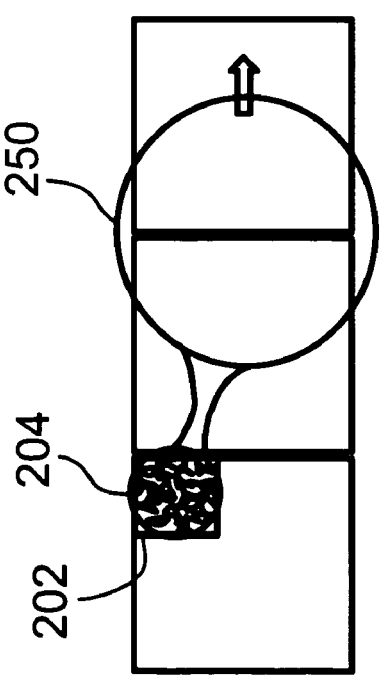
Figure 18(a)
Figure 18(b)
Figure 18(c)
Figure 18(d)

DROPLET-BASED CELL CULTURE AND CELL ASSAYS USING DIGITAL MICROFLUIDICS

CROSS REFERENCE TO RELATED U.S. APPLICATIONS

This patent application relates to, and claims the priority benefit from, U.S. Provisional Patent Application Ser. No. 61/064,002 filed on Feb. 11, 2008, in English, entitled DROPLET-BASED CELL ASSAYS, and which is incorporated herein by reference in its entirety.

FIELD OF THE INVENTION

The present invention relates to droplet-based cell assays and/or cell culture using digital microfluidics, and more particularly, the present invention relates to devices and methods used with those devices for performing cell assays and/or cell culture.

BACKGROUND OF THE INVENTION

The cell is the irreducible element of life and is often studied as a living model of complex biological systems. Cell-based assays are conventionally performed in well plates that enable simultaneous analysis of multiple cell types or stimuli. For such multiplexed analyses, cells in well plates are often evaluated using microplate readers, which can be integrated with fluid handling and other miscellaneous equipment in a robotic analysis platform. A major drawback of such systems is the expense of the instrumentation and the experimental consumables (e.g., plates, pipette tips, reagents, and cells). The latter is a particular disadvantage for cell-based assays as they are generally more complex and require larger amounts of reagents than cell-free assays.[1]

Recently, microfluidics has been touted as a solution for the challenges inherent in conducting multiplexed cell-based assays.[2] The conventional format for microfluidics, which is characterized by devices containing networks of micron-dimension channels, allows integration of multiple processes on a single platform while reducing reagent consumption and analysis time. There are numerous advantages of using microfluidic based systems for cell assays, some of which are self-similarity in dimensions of cells and microchannels (10-100 μm widths and depths), laminar flow dominance and formation of highly resolved chemical gradients, subcellular delivery of stimuli, reduced dilution of analytes, and favorable scaling of electrical and magnetic fields. For the last ten years, researchers have used microchannels to manipulate and sort cells, to analyze cell lysates, to assay intact-cell biochemistry, and to evaluate cell mechanical and electrical responses. In most of these studies, cells were exposed to one stimulus or to a limited number of stimuli. There have been just a few attempts to conduct multiplexed assays as it is difficult to control many reagents simultaneously in a complex network of connected channels, even when using microvalve architectures developed for microfluidic devices.[3] Finally, we note that there have been only a few microfluidic devices integrated to multiplexed detection instruments such as microplate readers;[4] we believe this will be a necessary step for the technology to become competitive with robotic screening systems.

A potential solution to the limitations of the channel-microfluidic format is the use of "digital" or droplet-based microfluidics. In digital microfluidics (DMF), discrete droplets containing reagents are manipulated by sequentially applying potentials to adjacent electrodes in an array.[5-14] Droplets can be manipulated independently or in parallel on a reconfigurable path defined by the electrode actuation sequence, which allows for precise spatial and temporal control over reagents. As with all microscale techniques, cross-contamination is a concern for DMF, but this phenomenon can be avoided by dedicating separate paths for each reagent. DMF has been used to actuate a wide range of volumes (nL to μL) and, unlike channel devices, there is no sample wasted in creating small plugs for analysis. In addition, each droplet is isolated from its surroundings rather than being embedded in a stream of fluid—a simple method of forming a microreactor in which there is no possibility that products will diffuse away. The preservation of products in a droplet is of great importance in cell assays targeting molecules secreted from cells into extracellular space. In addition, droplets provide mostly static fluid conditions without unwanted shear stress that is inevitable in continuous flow microfluidics. A further advantage of DMF is its capacity to generate nanoliter samples by translating droplets through selective wettability areas on an electrowetting-based platform.[15]

There is currently much enthusiasm for using DMF to implement multiplexed assays; however, it has only been applied to a few non-cell assays. To the inventors' knowledge, there are no reports of the use of DMF to analyze cells. There are a few studies demonstrating only dispensing and manipulation of droplets containing cells, cell sorting, and cell concentration on a DMF platform. WO 2007/120241 A2 entitled "Droplet-Based Biochemistry"[16] discloses dispensing and dividing droplets containing cells, generating droplets with single cells, detecting a type of cell, and sorting cells. US20070148763 A1 entitled "Quantitative cell dispensing apparatus using liquid drop manipulation"[17] describes cell droplet handling, to achieve a predetermined number of cells. In a journal paper by Fan et al,[18] dielectrophoresis was used to concentrate neuroblastoma cells within droplets on a DMF platform.

It would be very advantageous to provide droplet-based cell culture and/or assays using digital microfluidics in order to enable automated cell micro culture and high-throughput screening ability for cell analysis. DMF would also address some problems associated with standard culture and assaying in well-plates or in continuous-flow microfluidic devices.

SUMMARY OF INVENTION

The present invention provides embodiments of devices and methods for droplet-based cell culture and assays using digital microfluidic devices designed to manipulate, operate, and analyze cell-containing droplets. Cells in a suspension and cell-assay and/or cell-culture reagents are deposited in the device by either dispensing them from device reservoirs or dispensing them into the device using external means (e.g., pipette, robotic dispenser, etc.). In order to perform an assay with cells in suspension, cell-containing droplets and reagent-containing droplets are moved between adjacent electrodes by applying voltages to electrodes. General assay protocol comprises dispensing and translating droplets, merging and mixing droplets with cells and reagents at least once, possible splitting of droplets, incubating cells with reagents in merged/mixed (and split) droplets at least once, and detecting signal from cells in merged/mixed (and split) droplets in the device after final incubation. Using the same DMF techniques, suspended cells are also long-term cultured and split at regular time intervals.

Additionally, DMF devices are designed to culture and assay adherent cells. After being introduced in a device in suspension, adherent cells are seeded on cell culture sites (patterned DMF device surface for cell attachment), where they can be long-term cultured in droplets, subcultured using standard subculture protocols, and assayed. Media exchange and regent delivery on cell culture sites (CSSs) is performed using standard DMF operations: translating, merging, mixing and splitting droplets. In addition, a new technique, passive dispensing, is developed for more efficient delivery of reagents/media from big source droplet translating over CCSs. By means of DMF and passive dispensing, a first multigenerational cell culture in a microscale is realized.

Culture and assay reagents comprise chemical, biochemical and biological reagents. Droplets contain additives including pluronics and various hydrophilic polymers to facilitate cell-containing droplet actuation by preventing non-specific adsorption of cells and proteins to a device surface.

In a multiplexed assay, multiple cell-containing droplets (which may include one kind or multiple kinds of cells) are manipulated and assayed simultaneously or in a certain sequence with one or multiple reagents.

Thus, in an embodiment of the present there is provided method of performing droplet-based cell culture, comprising the steps of:

a) providing a digital microfluidic device comprising: an array of actuating electrodes formed on a substrate surface; and a coating formed on the substrate surface, the coating providing a working surface; wherein said actuating electrodes are connectable to an actuating electrode controller for exciting or de-exciting the actuating electrodes for translating liquid droplets over the working surface;

b) providing a cell-containing droplet at a location on the working surface, the cell-containing droplet containing cells and cell culture media;

c) incubating the digital microfluidic device in a controlled environment to culture the cells;

d) actuating electrodes of the array to dispense a droplet containing cell culture media to the cell-containing droplet; and e) incubating the digital microfluidic device in the controlled environment to further culture the cells.

In another aspect of the present invention there is provided a digital microfluidic device for conducting one or both of cell assays and cell culture, comprising:

a first substrate having a first substrate surface;

an array of actuating electrodes formed on the first substrate surface;

at least one dielectric layer formed on the first substrate surface covering each actuating electrode such that the actuating electrodes are electrically insulated from one another; and at least one reference electrode, wherein each actuating electrode is proximal to at least one of the reference electrodes;

an electrode controller capable of selectively exciting or de-exciting actuating electrodes for translating liquid droplets across a surface of the dielectric layer;

one or more first reservoirs in flow communication with the surface of said dielectric layer for holding at least one suspension of cells and one or more reagent reservoirs in flow communication with the surface of said dielectric layer for holding one or more cell assay reagents, cell culture reagents; and dispensing means for dispensing droplets of said at least one suspension of cells and droplets of said at least one cell assay reagents, cell culture reagents onto said surface of said dielectric layer; and a computer controller interfaced to said dispensing means and said electrode controller and being programmed to dispense droplets of the suspension of cells and droplets of said one or more cell assay reagents, cell culture reagents onto said surface of said dielectric layer and translating them over said array of actuating electrodes for mixing and optionally splitting said droplets in selected positions on said array of actuating electrodes to form one or more secondary droplets in a selected order defined by a selected cell assay protocol or cell culture protocol for which said computer controller is programmed.

A further understanding of the functional and advantageous aspects of the invention can be realized by reference to the following detailed description and drawings.

BRIEF DESCRIPTION OF THE DRAWINGS

Preferred embodiments of the invention will now be described, by way of example only, with reference to the drawings, in which:

FIGS. 7(a) to (f) show sequential images from a movie depicting a digital microfluidic cell-based assay;

FIGS. 11(a) to (d) are diagrammatic representations of seeding adherent cells in a DMF device where (a) shows actively dispensed droplet of cell suspension translating to a cell culture site (CCS), (b) shows passively dispensing a droplet of cell suspension onto the CCS from a source droplet, (c) shows cells in suspension seeded on the CCS, and (d) shows cell monolayer formed on the ECM substrate on the CCS;

FIGS. 18(a) to (d) show diagrammatic representations of assaying adherent cells in a DMF device where, (a) shows a monolayer of adherent cells cultured on a CCS in cell culture media, (b) washing cells and delivering assay reagents to cells via passive exchange, (c) incubating cells with assay reagents, and (d) detecting and analyzing cell response to assay stimuli.

DETAILED DESCRIPTION OF THE INVENTION

Without limitation, the majority of the systems described herein are directed to methods and devices for droplet-based cell assays using digital microfluidics. As required, embodiments of the present invention are disclosed herein. However, the disclosed embodiments are merely exemplary, and it should be understood that the invention may be embodied in many various and alternative forms.

The figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to droplet-based cell assays and culture using digital microfluidics (DMF).

As used herein, the term "about" and the symbol "~", when used in conjunction with ranges of dimensions, temperatures or other physical and/or chemical properties and/or characteristics is meant to cover slight variations that may exist in the upper and lower limits of the ranges of dimensions as to not exclude embodiments whereon average most of the dimensions are satisfied but where statistically dimensions may exist outside this region. For example, in embodiments of the present invention dimensions of a digital microfluidic device are given but it will be understood that these are not meant to be limiting.

Figure 1:
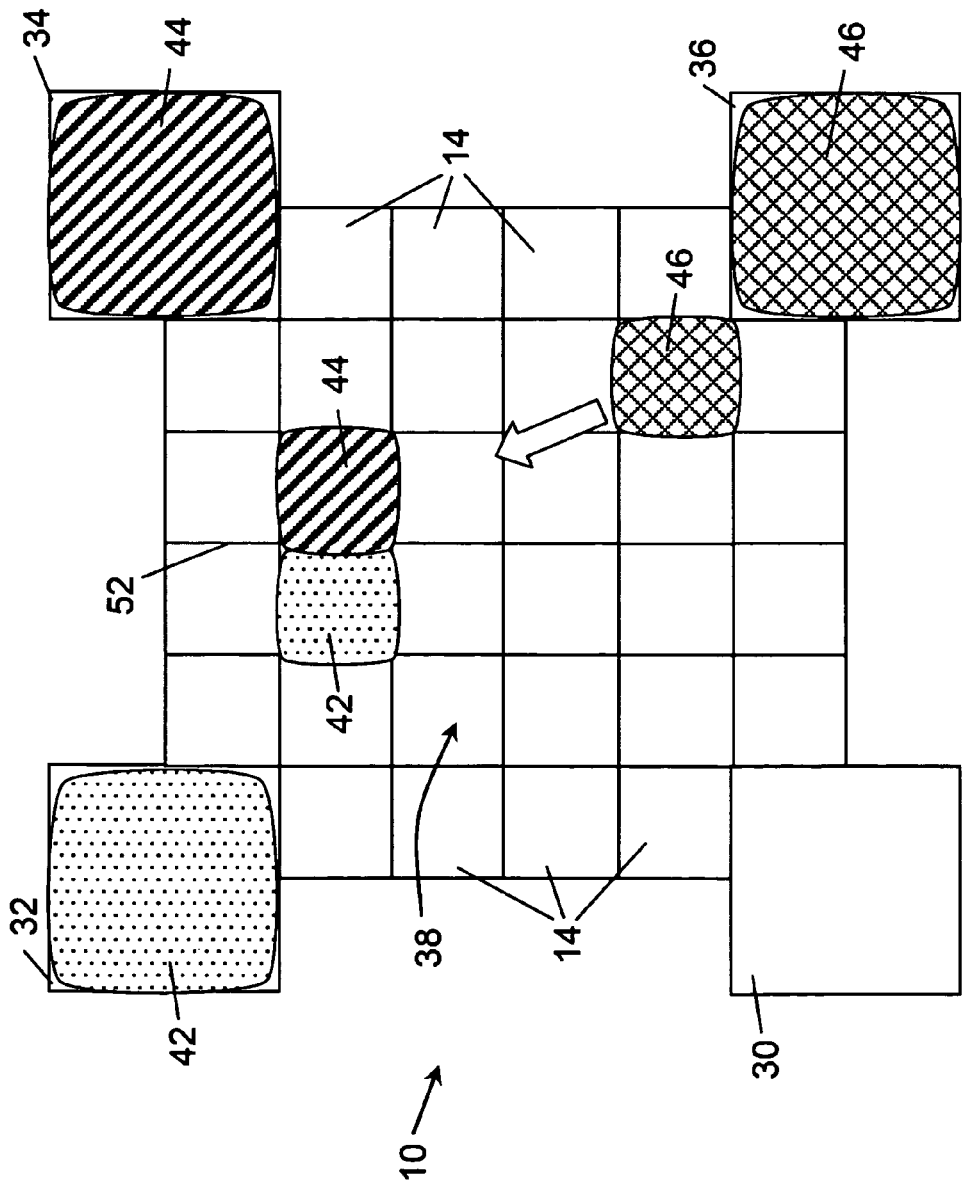
FIG. 1 is a top view of a complete digital-microfluidic device showing three droplet sources: cells, reagent, and dye.

FIG. 1 shows a top view of a microfluidic device shown generally at 10 which may be used for droplet-based cell culture and cell assays using digital digital microfluidics in accordance with the present invention. Reservoir electrodes 32, 34, and 36 store droplets 42, 44, 46 containing cells, reagent, and dye, respectively, and are capable of dispensing the liquids onto the center region 38 of the device. Small volumes of liquids are dispensed as droplets and translated by applying voltages to actuating electrodes 14. There is also another reservoir electrode 30 shown in the device in FIG. 1 which may be used as a reservoir as well.

Figure 2:
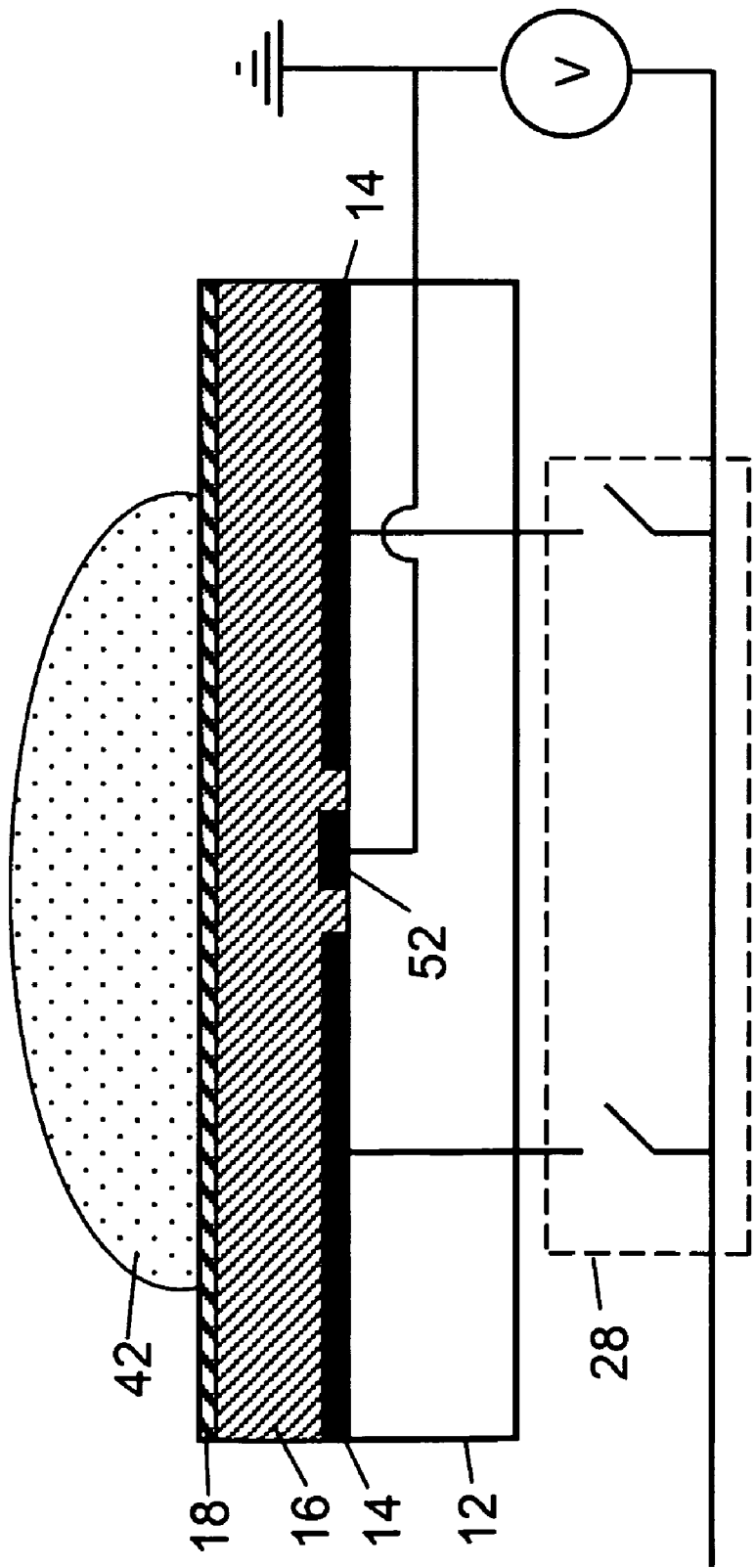
FIG. 2(a) shows a cross-sectional view of the device of FIG. 1.
FIG. 2(b) shows a cross sectional view of an alternative embodiment of the device of FIG. 1 which uses a one-plate design.

FIG. 2(a) is a cross-sectional view of a portion of the microfluidic device 10 of FIG. 1 showing two adjacent electrodes 14 of the electrode array. Electrodes 14 (10 nm Cr+, 100 nm Au) rest on a substrate layer 12 and are separated from each other by a dielectric material 16 (for example 2 μm Parylene-C). The device can have more than one dielectric layer 16. Located on top of dielectric material 16 is a hydrophobic layer 18 (for example Teflon AF, 50 nm). The array of actuating electrodes and exposed areas of substrate surface are thus covered by a working surface. Spaced above electrodes 14/dielectric layer 16 is a continuous reference electrode 22 coated on a substrate layer 24, and a hydrophobic layer 20 (for example Teflon AF, 50 nm) is coated on reference electrode 22. Alternatively, another dielectric layer can be deposited between layers 20, 22. Liquid droplets 42 rest in-between two hydrophobic layers 18 and 20. Electrodes 14, voltage source 26, and the continuous reference electrode 22 together form an electric field, digitally manipulated by controller 28. For droplet manipulation, reference electrodes 22 are biased to a potential different from the actuating potential. Commonly used reference potential is ground.

In a preferred embodiment of the present invention, the upper hydrophobic layer 20, reference electrode 22, and substrate layer 24 are substantially transparent to allow optical analysis of the assays. Furthermore, layers 20, 22, and 24 are not necessary to translate droplets.

While the present invention discusses the two-plate design of FIG. 2(a), a one-plate design is also possible, as shown in FIG. 2(b). In FIG. 2(b), layers 20, 22, and 24 are removed. Rather than have a dedicated reference electrode layer 22, the reference electrode is patterned adjacent to electrodes 14, forming a continuous grid 52 separated from electrodes 14 by dielectric material 16. The continuous grid 52 extends in both directions defining the plane in which electrodes 14 are located.

Reference electrodes can also be coplanar with the top surface of the dielectric layer. In a device with multiple dielectric layers, reference electrodes can be coplanar with the top surface of any dielectric layer, while being insulated from actuating electrodes 14. The design of reference electrodes is not limited to a grid, e.g. they can be in a form of a wire or an array similarly to electrodes 14.

FIG. 3 shows three frames from a movie wherein a 150 nL droplet 42 containing ~260 cells is dispensed from a reservoir of a microfluidic device with identical dimensions but fewer electrodes than the microfluidic device 10 shown in FIG. 1, wherein cells were labeled with a viability dye, calcein AM, which fluoresces green.

FIGS. 7(a) to (f) show sequential images from a movie depicting a digital microfluidic cell-based assay, wherein a 150 nL droplet 42 containing ~525 cells was dispensed (a, 402), translated (b, 404), and merged (c, 406) with a 150 nL droplet 44 of Tween 20 dispensed (b, 402) from a second reservoir. The merged droplet was actively mixed (408) on four neighboring electrodes (d); after 20 min incubation in a humidified environment, the combined droplet was merged (e, 406) and mixed (e, 408) with a 150 nL droplet 46 containing viability dyes. The final droplet was incubated (f, 410) for 20 minutes in a humidified environment.

Figure 7B:
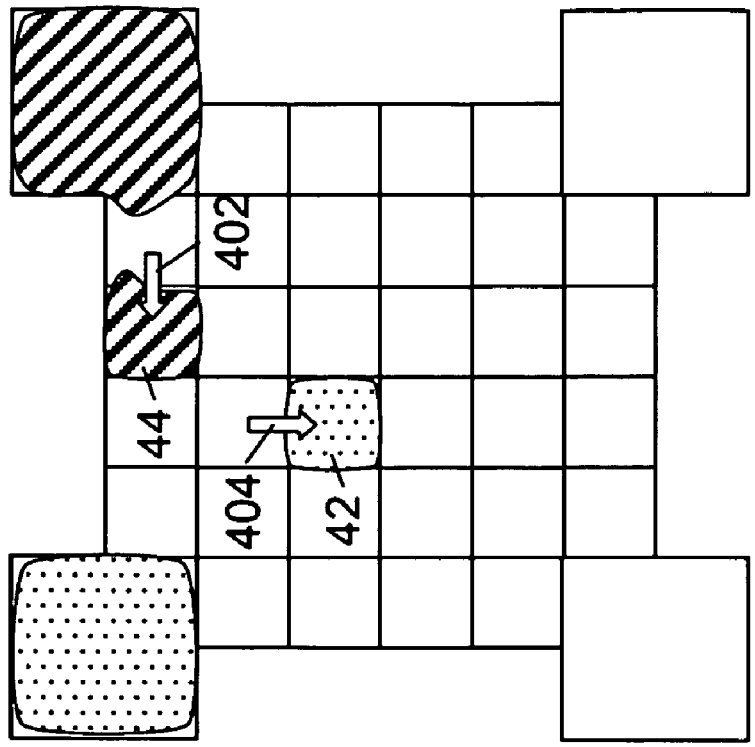
Figure 7A:
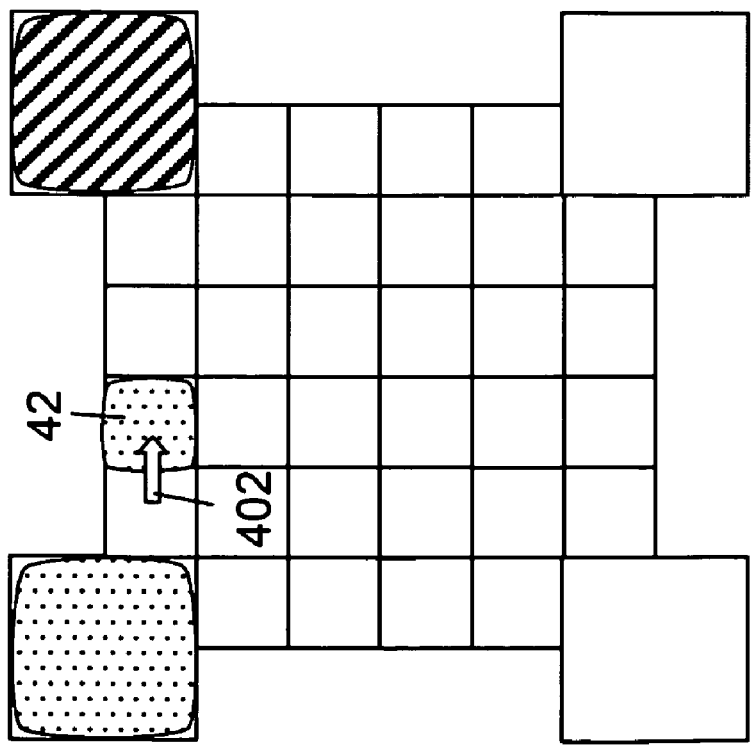
Figure 7F:
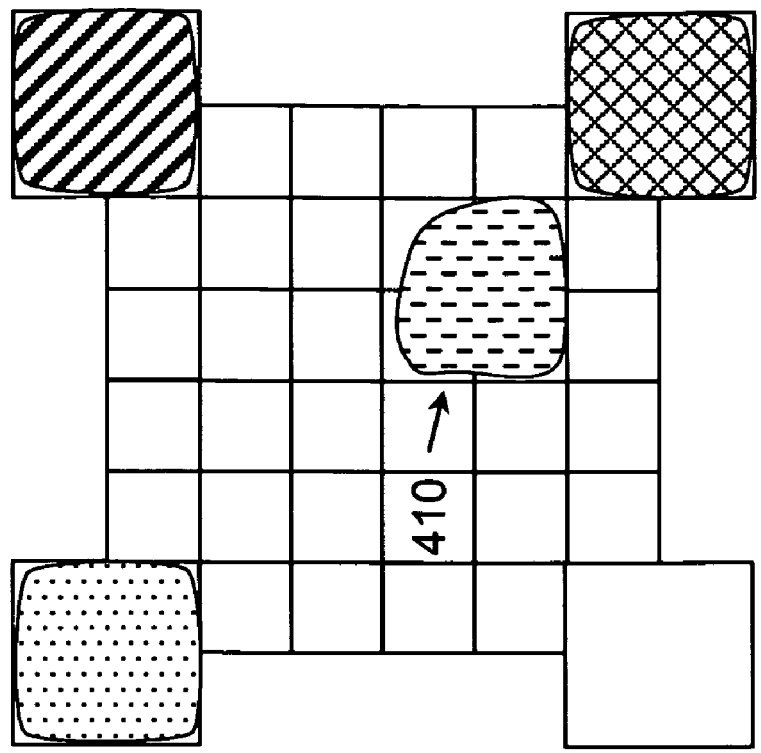
Figure 7E:
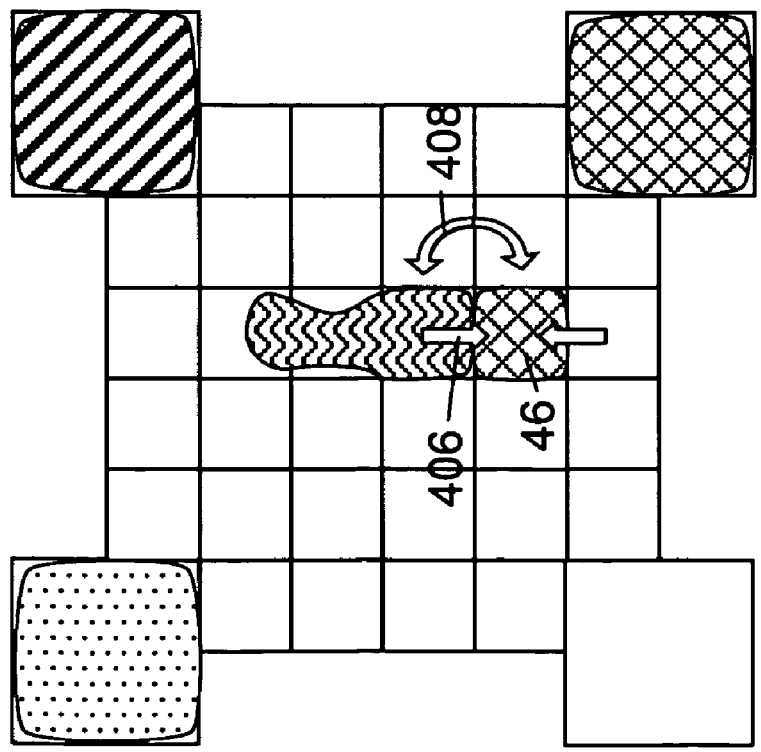
Figure 8A:
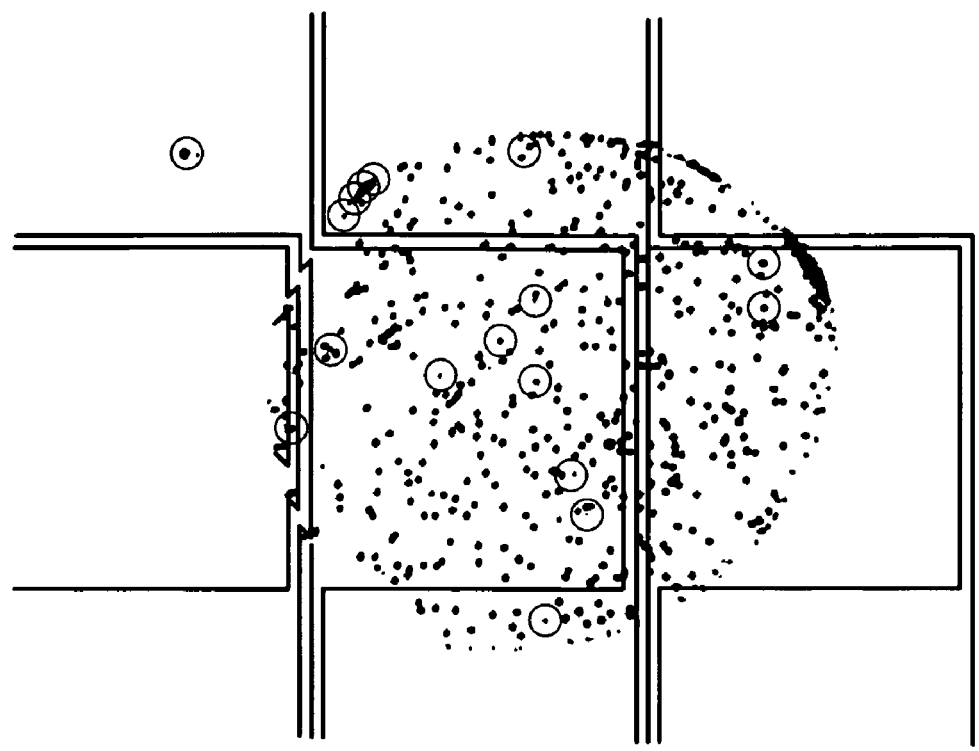
FIGS. 8(a) and (b) show fluorescent images of droplets with cells treated with (a) 0% and (b) 0.5% Tween 20 and stained with viability dyes. (calcein AM and ethidium homodimer-1); in the droplet (a), almost all cells were live (dead cells in (a) are marked with small circles), and in the droplet (b), all cells were dead.

A sample result of the microfluidic cell-based assay of FIG. 7(f) is shown in FIGS. 8(a) and (b), wherein fluorescent images of droplets treated with (a) 0% and (b) 0.5% Tween 20. Calcein AM (green) was used to stain live cells, and ethidium homodimer-1 (red) for dead cells. In the former droplet (a), almost all cells were live (dead cells in (a) are marked with small circles), and in the latter (b), all cells were dead.

While digital microfluidics has been used previously to manipulate and evaluate a wide range of liquids and reagents, we report herein the first application of digital microfluidics to transport, analyze and culture biological cells. Using the parameters reported in the experimental section (elaborated below), cell suspensions representing a wide range of concentrations (including very dense solutions of $1 \times 10^8$ cells/mL) were found to be feasible to be actuated by DMF, with no differences observed in velocity or reliability relative to liquids not containing cells.

Figure 3A:
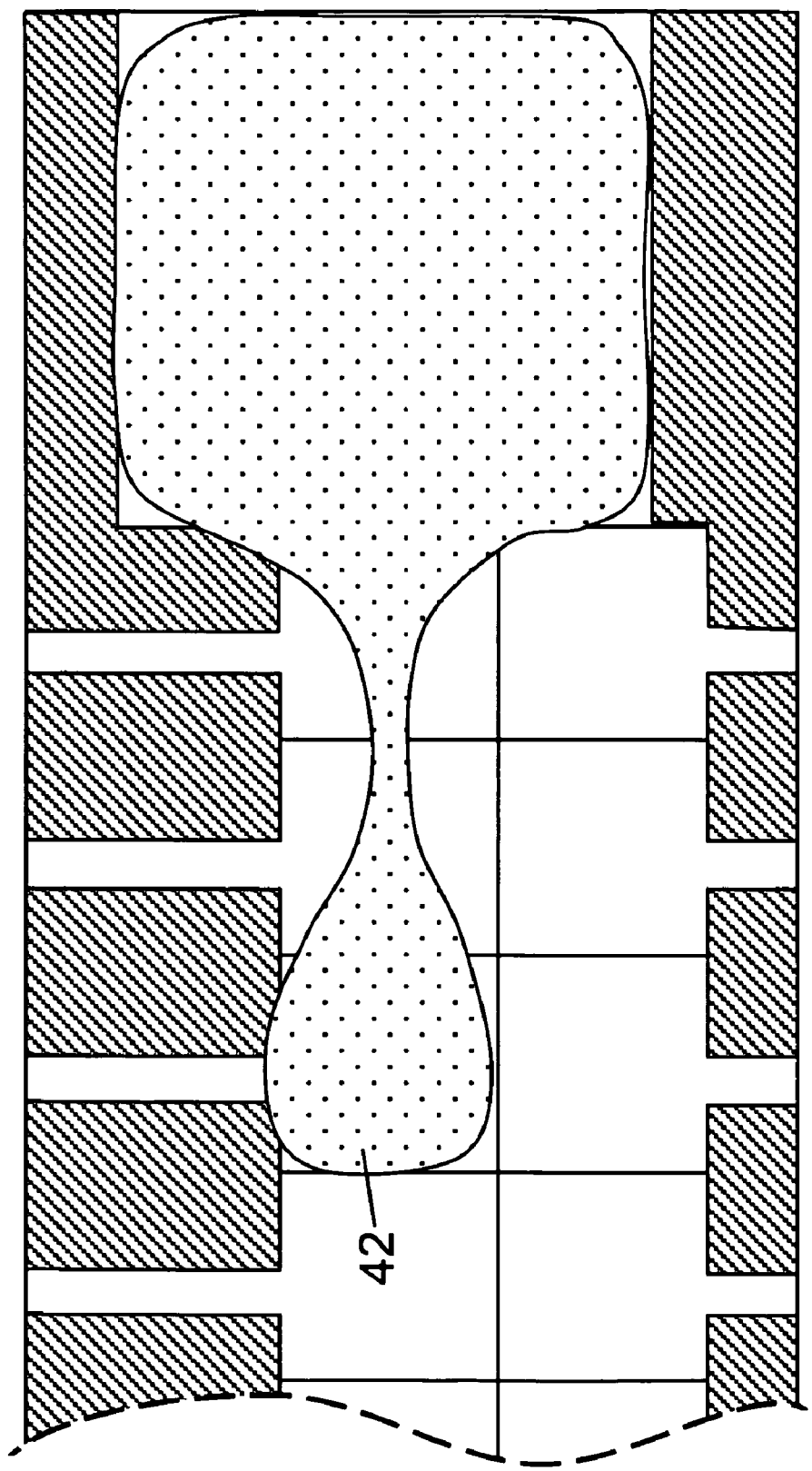
FIGS. 3(a) to (c) show three frames from a movie wherein a droplet with cells is dispensed from a reservoir.
Figure 3B:
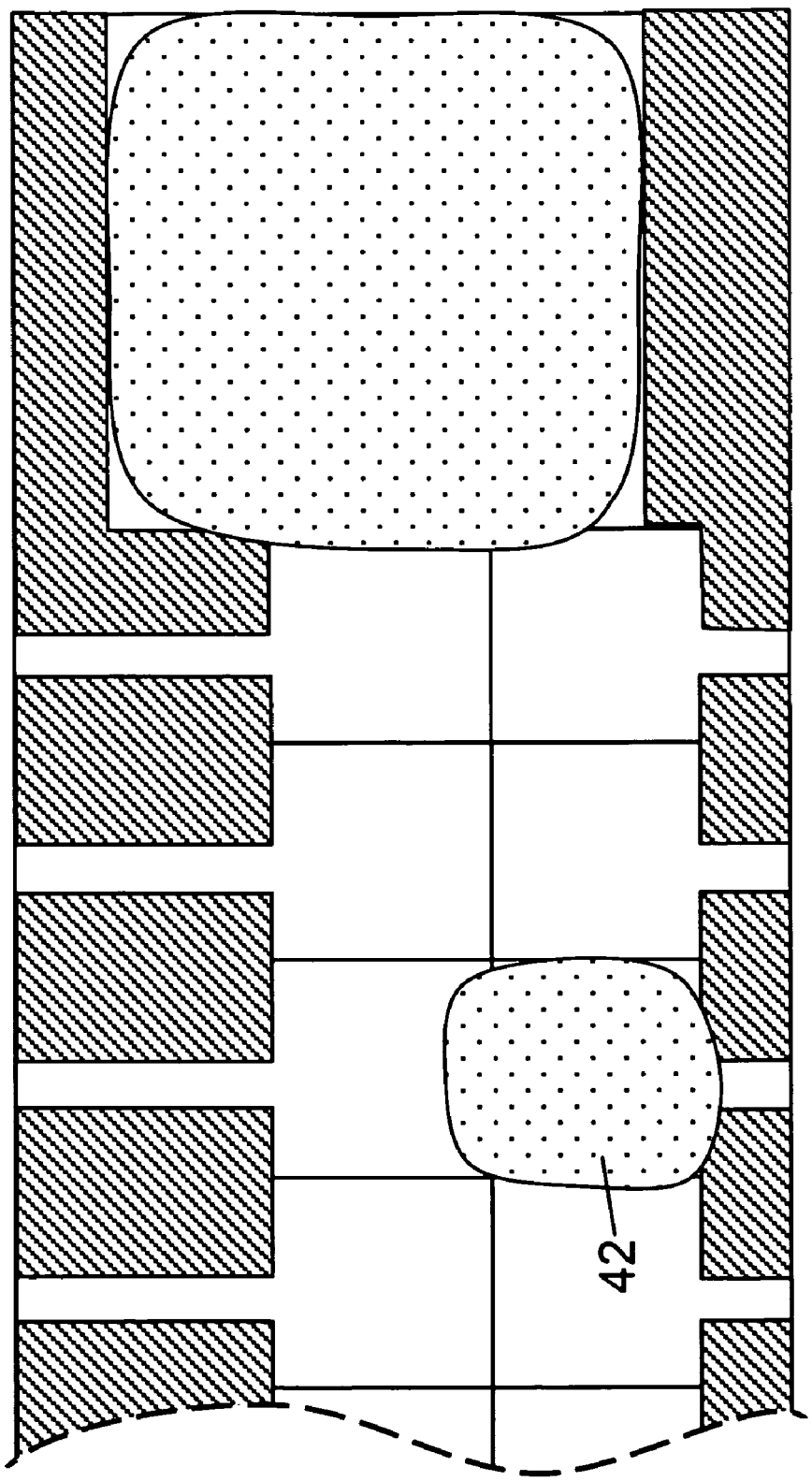
Figure 3C:
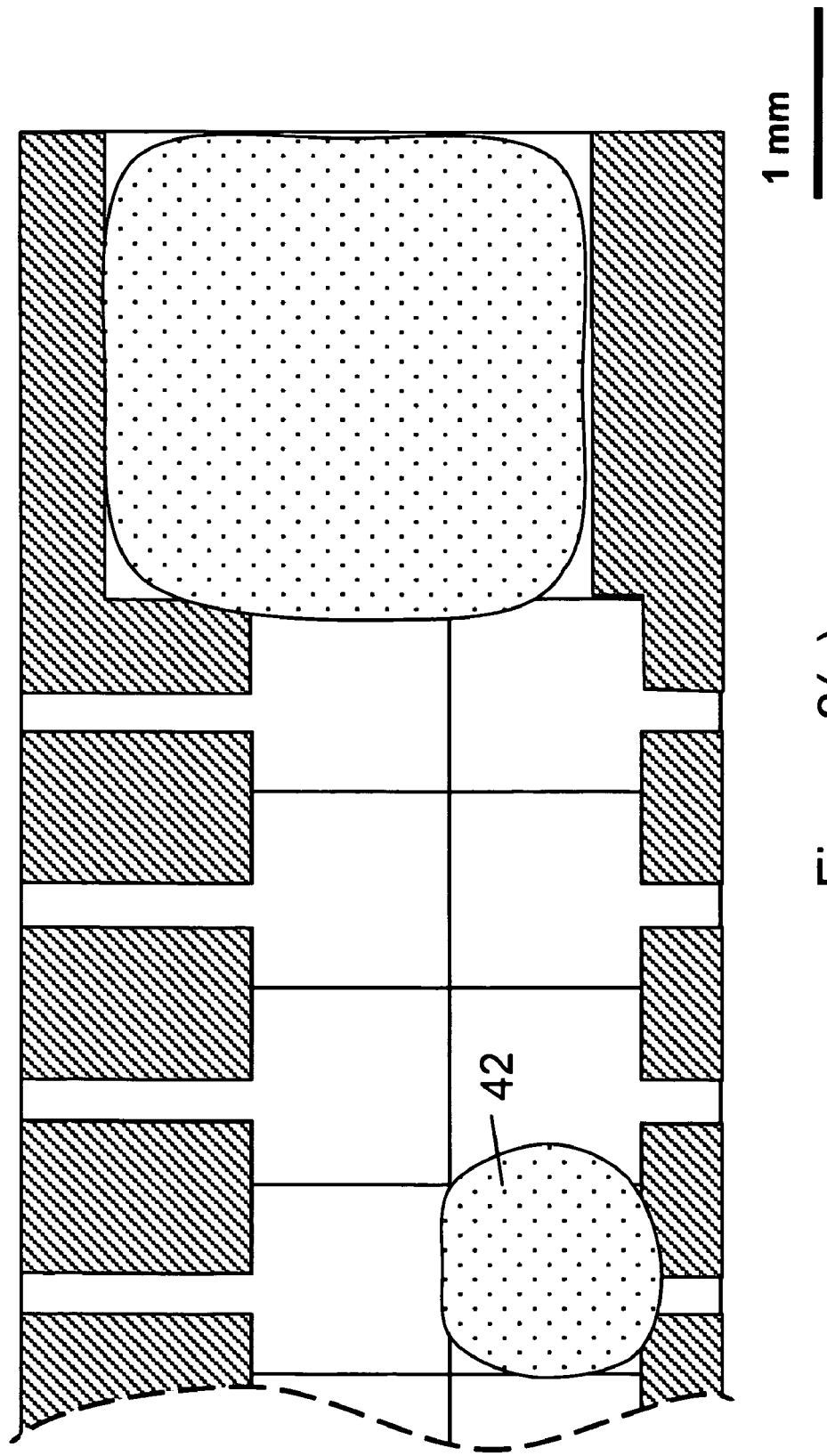

For example, FIGS. 3(a) to (c) depict a routine operation in our experiments: dispensing of a 150 nL droplet containing ~260 Jurkat T-cells. However, in initial work (with un-optimized parameters), droplets containing cells were difficult to manipulate, as cells tended to stick to the surface of the devices, causing contact line pinning. This problem was overcome by the use of the non-ionic surfactant, pluronic F68, which when used as a solution additive, facilitated actuation of suspensions of cells in all liquids tested (including PBS and complete media containing 10% fetal bovine serum).

Pluronics are block copolymers formed from poly(propylene oxide) (PPO) and poly(ethylene oxide) (PEO), and are commonly used as surface coatings for preventing non-specific protein adsorption. In our work, we used pluronics in solution, rather than as a surface coating; we hypothesize that in this configuration, the polymer coats cells and proteins in a manner such that their functionality is retained, but adsorption to hydrophobic surfaces is minimized. We note that pluronic F68 has been used extensively in cell-based assays with no evidence for detrimental effects on cell vitality,[19,20] and it is even used as a constituent in commercial cell growth media.[21] Our experiments support this trend—Jurkat T-cells incubated in medium containing 0.2% (wt/vol) F68 for 4 days (humidified incubator, 5% CO2, 37° C.) had identical growth rates and morphology as cells grown in media without pluronics. In on-going work, the optimal conditions (concentration and type of pluronic, etc.) for reducing unwanted adsorption in DMF are being evaluated; we used F68 for all of the results reported here.

A second challenge for using DMF for actuation of cells is droplet evaporation, which raises the concentration of salts and other buffer constituents, making the solution hypertonic. In the work described here, we controlled evaporation by positioning devices in a humidified atmosphere when not actively manipulating droplets by DMF. For the duration of the assay experiments (up to a few hours), such measures prevented significant evaporation, and no negative effects on cell viability were observed. For culturing cells, devices were placed in cell culture incubators at 37° C. and 5% $CO_2$. The DMF devices may be contained in a sterile, humidified chamber for the full duration of the assay or cell culture process (including actuation, incubation, and analysis) or culture which facilitates long-term cell culture and examination.

Effects of DMF Manipulation on Cell Vitality.

Digital microfluidic devices use electrical fields to actuate droplets, which led us to investigate the effects of droplet actuation on cell vitality. As described above, droplets are translated by an energized actuating electrode 14 on a bottom plate and a reference electrode 22 on a top plate (FIG. 2(a)). It should be noted that the reference electrode may also be placed on the bottom plate, as in reference electrode 52 (FIG. 2(b)). Because of the high conductivity of a droplet 42 of phosphate buffered saline (PBS) relative to the insulating dielectric layer 16 formed from Parylene-C, the inventors believe that cells would experience negligible electrical field upon application of driving potentials. This hypothesis was supported by a numerical simulation using the COMSOL Multiphysics 3.3a analysis package. In a simulation, shown in FIG. 4, in which 100 V was applied between top and bottom electrodes, the potential drop in the droplet was found to be only $3.73 \times 10^{-8}$ V, or 0.00000004% of the applied potential. Thus, it is contemplated that one would expect to observe modest effects (if any) on the vitality of suspensions of cells, upon application of electrical field. These effects were evaluated by three tests, measuring cell viability, proliferation, and biochemistry.

Figure 5:
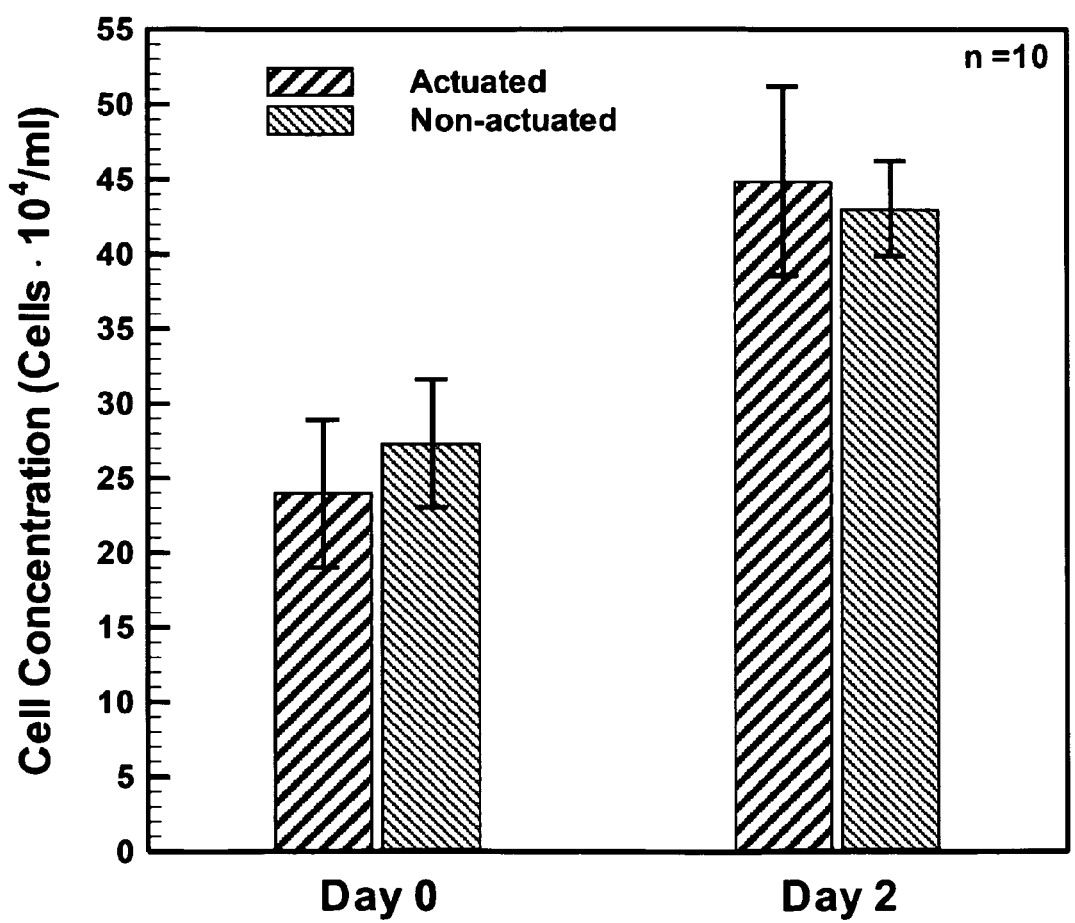
FIG. 5 is a graph of viability and proliferation tests for cells actuated by digital microfluidics showing no significant differences between the actuated and non-actuated cells.

As shown in FIG. 5, the viability of actuated and non-actuated cells was compared immediately after actuation, and proliferation was measured after 48-h incubation in a humidified incubator. There was no significant difference between actuated and non-actuated cells (P=0.11 for the viability assay, P=0.43 for the proliferation assay).

Figure 6A:
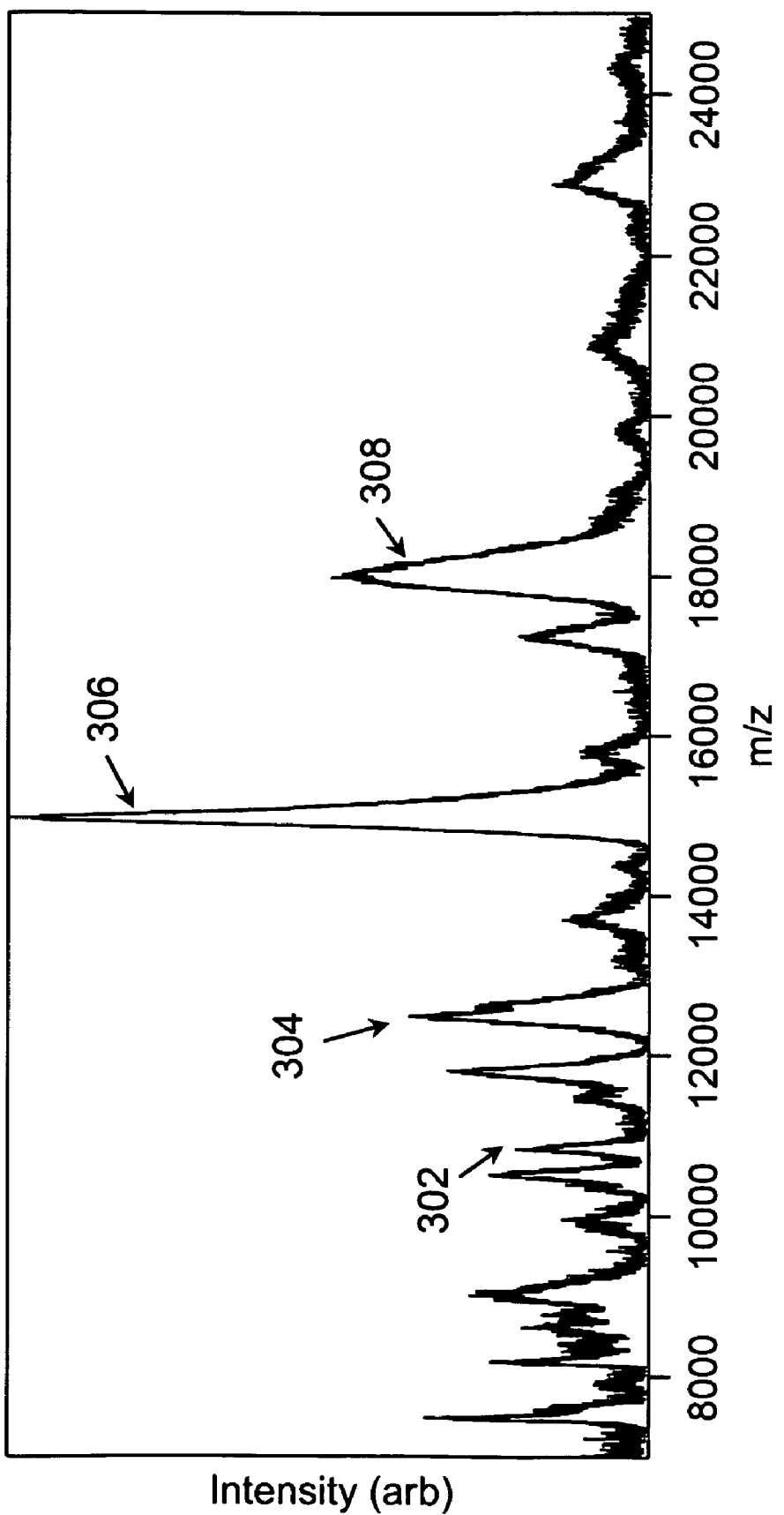
FIGS. 6(a) and (b) are graphs of vitality tests wherein cells in droplets were actuated, lysed, and analyzed by Matrix Assisted Laser Desorption Ionization Mass Spectrometry (MALDI-MS) showing no major qualitative differences between the (a) actuated and (b) non-actuated cells.

Cell biochemistry was evaluated qualitatively by analyzing lysates with MALDI mass spectrometry. FIGS. 6(a) and (b) show spectra of lysates of actuated cells and non-actuated cells, respectively. From previous studies of protein content in Jurkat T-cells,[22] we tentatively assigned several peaks, including heat shock protein (HSP10) 302, macrophage migration inhibitory factor 304, epidermal fatty-acid binding protein (E-FABP) 306, and peptidyl-prolyl cis-trans isomerase A 308. As shown, there are no major qualitative differences between the two spectra, which suggests that actuation by DMF does not cause catastrophic effects on cell biochemistry. We note that MALDI-MS is not a quantitative analysis technique (i.e., peak heights can vary considerably within multiple spectra of a single sample) The gene expression of T-cells and other cell types using quantitative PCR or gene microarray would be more appropriate quantitative techniques.

Cell Phenotype Assays by DMF.

Figure 8B:
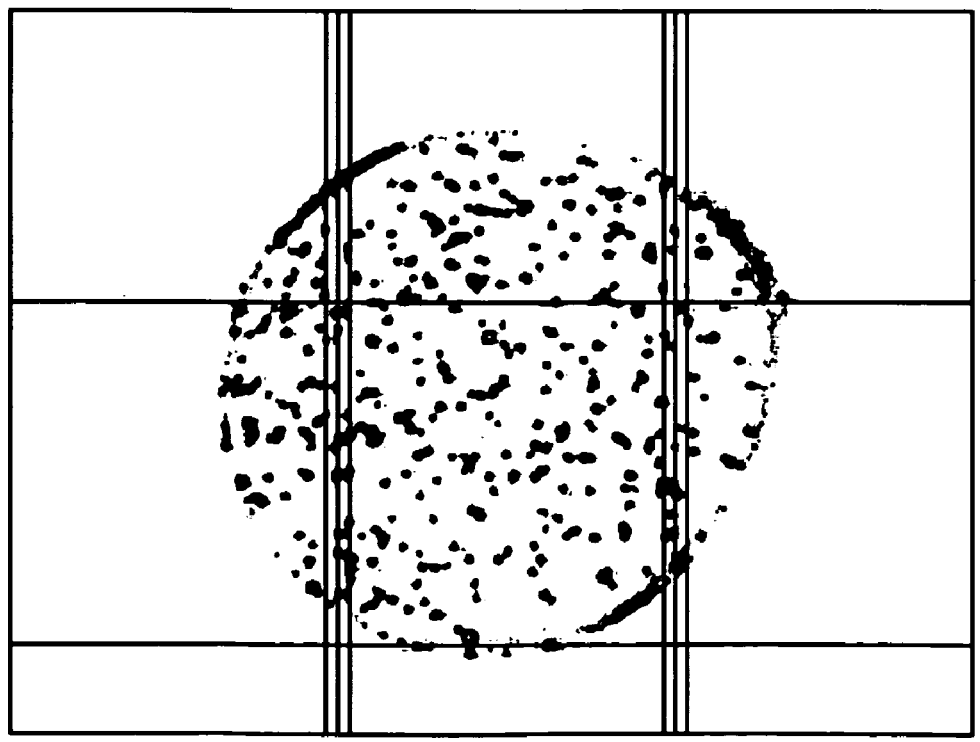

To illustrate that DMF is compatible with phenotypic assays, a dose-response toxicology screen was performed using Jurkat T-cells, shown in FIGS. 7 and 8. Cells were exposed to varying concentrations of the surfactant, Tween 20 (0.002% to 0.5% (v/v)) (FIG. 7) and then stained with viability dyes (FIG. 8). The complete assay, from droplet dispensing to the final incubation with dyes was performed on-chip. 150 nL droplets (~1 mm in diameter) were dispensed via DMF, and after merging and incubation, resulted in a final ~450 nL droplet (~1.8 mm diameter, 150 µm height). An equivalent assay was implemented in a 384-well plate with the same number of cells (~525 cells/well or droplet) but different sample volume. In the well-plate assays, 5 µL aliquots of each reagent were pipetted into conical wells (3.3 mm top-, 2 mm bottom diameter) resulting in a final volume of 15 µL (~5 mm height) which is in the recommended range for 384-well plates. Hence, well plates required ~30-fold greater reagent use than DMF, leading to a much lower cell concentration in the wells. As described below, this had significant effects on assay sensitivity.

Figure 9A:
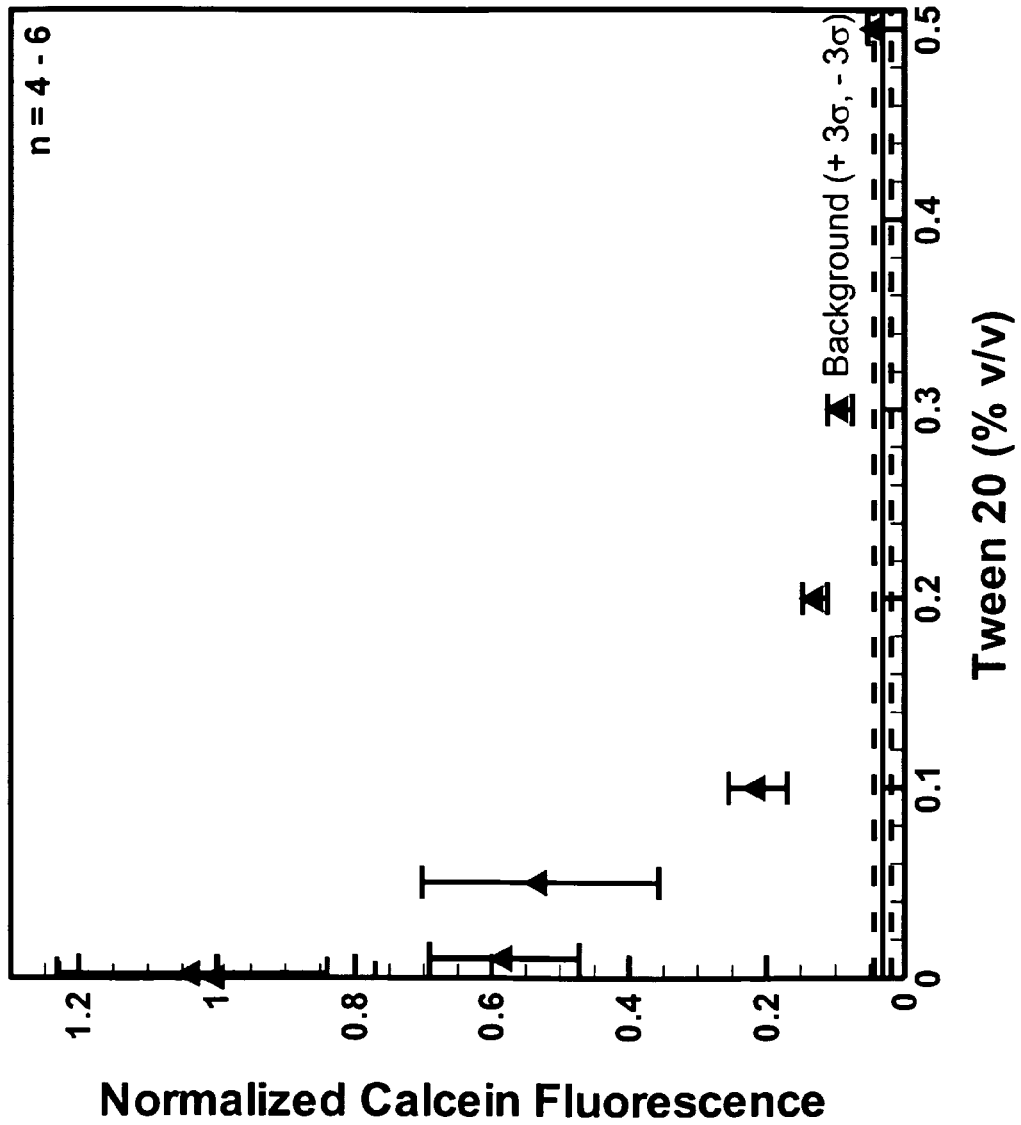
FIGS. 9(a) and (b) show two dose-response curves for Jurkat T-cells exposed to Tween 20 (0.002% to 0.5% (v/v)) using (a) a digital microfluidics assay and (b) a well-plate assay.
Figure 9B:
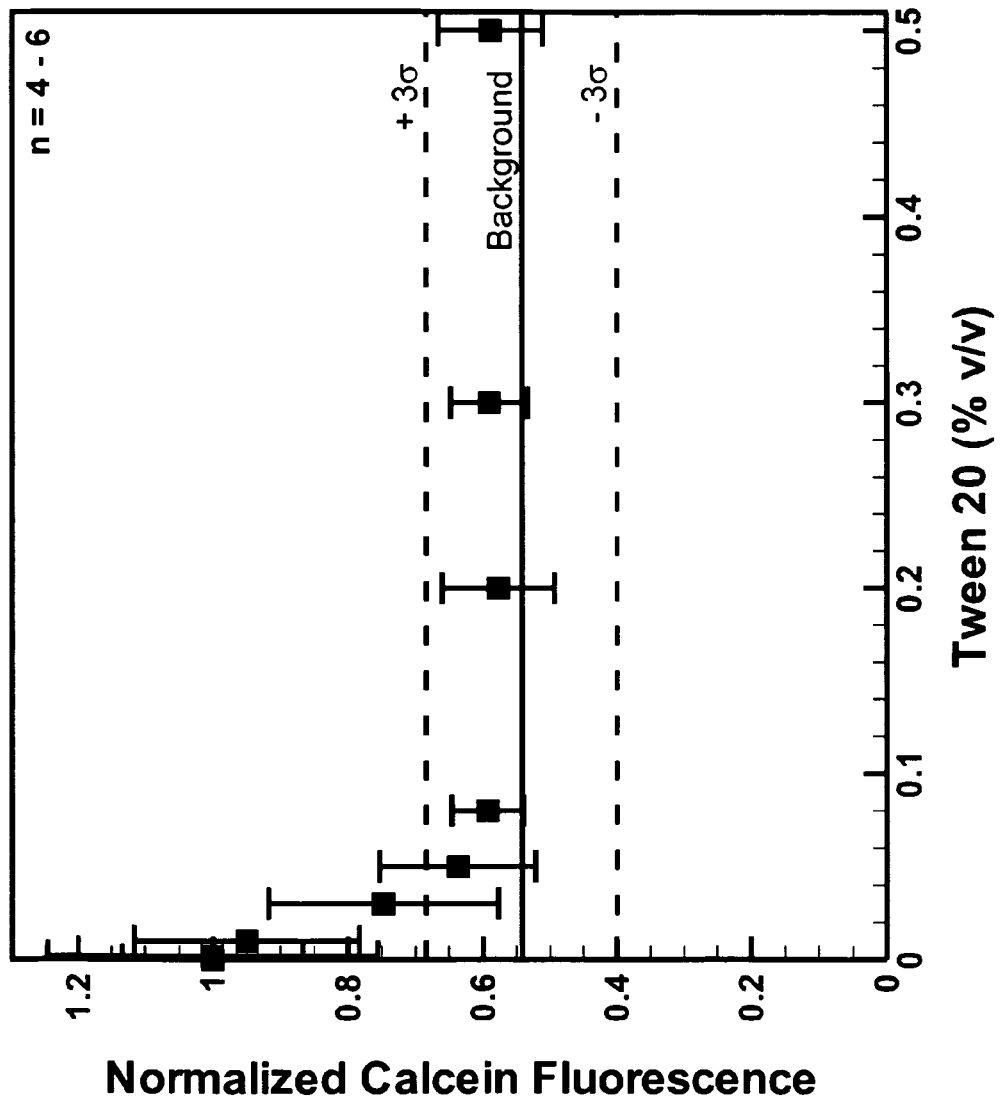

A fluorescence microplate reader was used to generate dose response curves for DMF and well plate assays using identical settings (FIG. 9, error bars are 1 standard deviation). As shown in FIG. 9, the DMF assays (a) had much lower background signals than the well-plate assay (b), resulting in a much larger signal-to-noise ratio than the well-based assays (b). As a consequence, the lowest detectable number of live cells in droplets was ~10 (a), compared to ~200 cells in wells (b). The latter value matches the general limits of detection listed by the manufacturer for such assays. One consequence of this difference was the determination of different 100%—lethal concentrations of Tween 20: ~0.5% (v/v) from the DMF assay and ~0.03% (v/v) from the well plate assay. The true 100%-lethal concentration was determined empirically by staining cells exposed to varying concentrations of Tween-20 and counting them using a hemacytometer. At the concentrations evaluated here, the fluorescence microplate reader results generated by the digital microfluidic method (a) were found to be a much better approximation of the empirical value than the conventional method (b). Thus, in this assay, the conventional method over-estimates the toxicity of Tween 20 by more than 15-fold; this is important, as cytotoxicity is widely used by regulatory agencies in initial screens for determining acceptable exposure limits, and by the pharmaceutical industry in early drug discovery.

Another cause of the improved sensitivity in droplet-based assays is the high cell concentration in ~nL droplets. The same number of cells in μL aliquots results in a much lower concentration and therefore, lower signal-to-noise ratio. In this experiment, 525 cells yielded $1.2 \times 10^6$ cells/mL in droplets, but only $3.5 \times 10^4$ cells/mL in wells. In addition, the cross-sectional density of cells in droplets was higher because of the slightly smaller droplet diameter (~1.8 mm) relative to that of the conical wells (2 mm bottom, 3.3 mm top). If it is assumed that all cells settled to the bottom of each well or droplet, then the same number of cells was distributed over an area that was ~20% smaller in droplets relative to wells, resulting in a higher signal. It is possible that all cells sedimented in droplets (150 μm height), while not all cells sedimented in wells (~5 mm height). If this were the case, it would obviously contribute to the observed differences in detection limits.

It should be noted that while the assay described above involved dispensing, translating, merging and mixing of droplets, other embodiments of cell assays and cell culture in DMF devices can include droplet splitting. Droplet splitting is implemented to reduce a droplet size, number of cells in a droplet, etc.

Some cell assays target molecules that cells secrete into their microenvironment, such as growth factors, signaling molecules, and metabolic products. Since DMF droplets of cell suspension are precise, confined volumes where all cell products are preserved, they are ideal microenvironment for extracellular biochemistry assays. In these assays, signal is detected from a suspension medium rather than cells. Suspension medium can be analyzed by immunoassays or other means. Droplets of cell suspension can alternatively be removed from a DMF device and analyzed externally.

The results presented above demonstrate assaying population of cells of one kind; nevertheless, it is also possible to assay droplets containing multiple kinds of cells (e.g., different cell types, or different phenotypes of the same cell type). Droplets with multiple kinds of cells can be generated by either dispensing them from reservoirs containing the same mixed population of cells, or by combining droplets containing one or several kinds of cells. Combining droplets, merging and mixing, results in larger droplets which can be split in droplets of desired size.

Concentration of cells in a droplet can be controlled by the concentration of cells in a source (a device reservoir or an external reservoir) or by combining droplets of suspended cells with droplets of cell suspension medium. In this way, concentration of cells is reduced by the ratio of the combined volumes. Combined droplet can be split in smaller droplets which can be further merged with cell suspension medium for additional cell concentration reduction. By repeating the procedure above, droplets with single cells can be generated and used in single-cell assays.

The results described above demonstrate that DMF can be used to implement cell-based assays with very high performance. With reduced reagent and cell consumption, and automated liquid manipulation, DMF devices outperformed standard well plate assays, and resulted in significant improvements in assay sensitivity. The above results clearly demonstrate the efficacy of c DMF cell-based assays for phenotypic screening.

Cells in Suspension Culture

Cell culture entails growing cells in a growth medium under controlled temperature and atmosphere conditions. For example, mammalian cells are grown in humidified atmosphere at 37° C. and 5% $CO_2$, in cell culture incubators. Growth medium supplies nutrients and growth factors to cells; its ingredients are cell type dependant. In standard cell culture, cells grow suspended in milliliter volumes in cell culture flasks; they are split/subcultured every 2-3 days and resuspended in a fresh growth medium.

In one embodiment of this invention we demonstrate: (1) growing cells in nanoliter-microliter droplets in DMF devices (in a cell culture incubator), (2) changing media daily, and 3) splitting cells every 2-3 days. Media change involves adding one or more droplets of fresh media to a droplet of incubated cells and thereby partially replenishing growth media. Cells are further incubated in the combined droplet or in smaller droplets generated by splitting the combined droplet. Cell subculture or splitting is achieved similarly to media change by combining (merging and mixing) a droplet of incubated cells and a droplet of fresh media, splitting the combined droplet, and repeating this procedure using the split droplet(s) until a desired cell concentration is reached. Final droplets are then incubated, while other droplets of suspended cells generated in the subculturing process are discarded.

Multiplexed Cell Culture/Cells Assays

Figure 10:
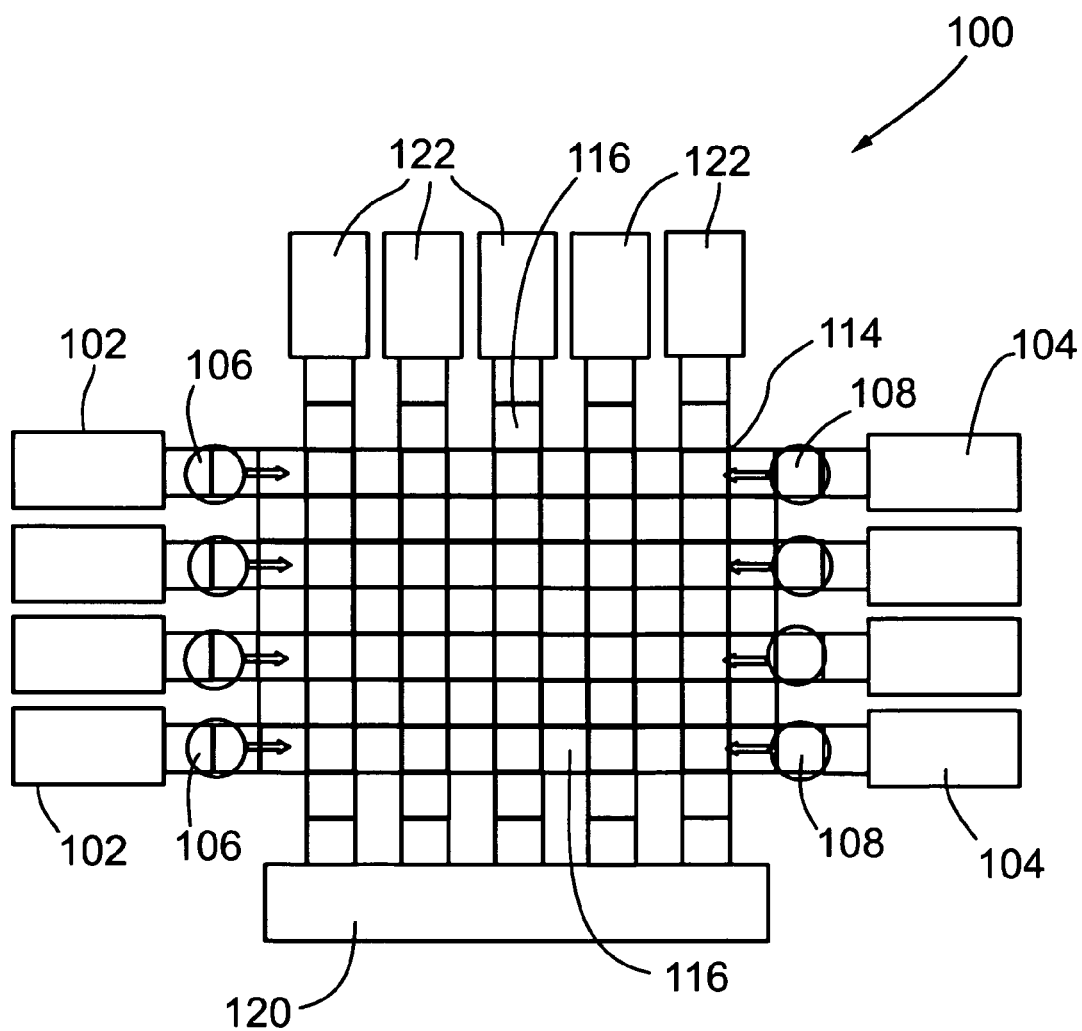
FIG. 10 shows a top view of an embodiment of a DMF device for multiplexed cell assays which comprises reservoirs for four different cell suspensions and nine different assay reagents, and a waste reservoir.

In a multiplexed assay 100 (shown in FIG. 10), multiple droplets 106 containing one kind or multiple kinds of cells are exposed to droplets 108 containing one or multiple reagents 104 and are assayed similarly to the assays described above. Cells in a suspension and cell-assay reagents can be deposited in the device either by dispensing them from device reservoirs 102 (cells) and 104 (reagents) or by dispensing them using external means (e.g., pipette, robotic dispenser, etc.), not shown herein. A multiplex device, an example of which is shown in FIG. 10, can also be used for multiplex cell culture, where cells can be grown and maintained in multiple droplets.

There are several ways of configuring the reservoirs. In one configuration of the method and system the reservoirs may be external to digital microfluidic device and include for example arrays of pipettes, robotic dispensers, microprinters and microstamps. Alternatively, the reservoirs could be integrated as part of the digital microfluidic device, which are in flow communication with the hydrophobic/dielectric surface above the array of actuating electrodes. The reservoirs can be containers integrated as part of the digital microfluidic device. Alternatively they may include actuating electrodes from said array of actuating electrodes modified to act as the liquid reservoirs as shown in FIG. 1 where reservoir electrodes 32, 34, and 36 store droplets 42, 44, 46 containing cells, reagent, and dye, respectively.

The reservoirs could be part of a cartridge assembled with the digital microfluidic device which is in flow communication with the hydrophobic/dielectric surface above the array of actuating electrodes.

The droplets are then translated to pre-selected sites on the top surface of the substrate 114 on which the array of actuating electrodes 116 is located. Assays in multiple droplets are performed simultaneously or sequentially in a certain order defined by the cell assay protocol. For example, a computer controller interfaced to the device reservoirs and associated dispensing devices is programmed to dispense droplets of the suspension of cells and droplets of one or more cell assay reagents onto the top surface of the dielectric layer covering the electrode array 116 and surface of the substrate 114, and translating them over said array of actuating electrodes for mixing the droplets in selected positions on the array of actuating electrodes to form one or more secondary droplets in a selected order defined by a selected cell assay protocol for which said computer controller is programmed.

Signals from secondary droplets are detected using multiplexed detection instruments such as optical sensors, optical detectors comprising a light source and a photodetector, optical detectors that measure absorbance, fluorescence, epifluorescence, chemiluminescence, UV light detector, radiometric detector, scanning, imaging, and confocal microscopy detectors, CCD cameras, and microplate readers. The detection step is to detect or identify any reaction products formed by the cell assay, or to identify, monitor and count the cells if a cell culture is being performed to mention just a few.

The detection step may be conducted by first translating the secondary droplet(s) to one or more selected positions on the substrate surface for analysis or the secondary droplet(s) may be removed from the device and analyzed externally.

All waste liquid droplets generated during the assay are translated to the waste container 120. Reservoirs 122 may contain wash solutions for cleaning the surface of the device between assays.

Experimental

The use of the digital microfluidics for conducting droplet-based cell assays using digital microfluidics will now be illustrated with the following non-limiting examples/studies. More particularly, herebelow, it is shown experimentally that the effects of actuation by digital microfluidics on cell vitality are minimal, and in addition, it is shown that a cytotoxicity assay implemented by DMF has much better sensitivity than macroscale methods, which suggests applications in regulatory policy and in drug discovery. It is also demonstrate compatibility of DMF cell assays with fluorescence microplate reader detection. This technique has great potential as a simple yet versatile analytical tool for implementing cell-based assays on the microscale.

Reagents and Materials.

Unless otherwise indicated, reagents used outside of the clean room were purchased from Sigma-Aldrich (Oakville, ON), and cells and cell culture reagents were from American Type Culture Collection (ATCC, Manassas, Va.). Fluorescent dyes were from Invitrogen-Molecular Probes (Eugene, Oreg.), Parylene-C dimer was from Specialty Coating Systems (Indianapolis, Ind.), and Teflon-AF was purchased from DuPont (Wilmington, Del.). Clean room reagents and supplies included Shipley S1811 photoresist and MF-321 developer from Rohm and Haas (Marlborough, Mass.), solid chromium and gold from Kurt J. Lesker Canada (Toronto, ON), standard gold etchant from Sigma-Aldrich, CR-4 chromium etchant from Cyantek (Fremont, Calif.), AZ-300T photoresist striper from AZ Electronic Materials (Somerville, N.J.), and hexamethyldisilazane (HMDS) from Shin-Etsu MicroSi (Phoenix, Ariz.). Concentrated sulfuric acid and hydrogen peroxide (30%) were from Fisher Scientific Canada (Ottawa, ON), and piranha solution was prepared as a 3:1 (v/v) mixture of sulfuric acid and hydrogen peroxide.

Cell Culture.

Jurkat T-cells (human leukemia lymphocytes) were maintained in a humidified atmosphere (5% $CO_2$, 37° C.) in RPMI 1640 medium supplemented with 10% fetal bovine serum (Invitrogen Canada, Burlington, ON), penicillin (100 IU/mL), and streptomycin (100 µg/mL). Cells were subcultured every 3-4 days at ~1×10$^6$ cells/mL. A working buffer of 0.2% (wt/v) pluronic F68 (Sigma-Aldrich) in Dulbecco's phosphate buffered saline (PBS) (Invitrogen Canada) was used for most cell-based assays. Prior to experiments, cells were washed three times in PBS, suspended in 0.2% F68 (wt/v) in PBS at $3.5×10^6$ cells/mL, and then incubated at room temperature (1 h). Cell numbers and viability were quantified using a hemocytometer and trypan blue exclusion (Invitrogen Canada) immediately prior to all experiments. Prior to cell viability/proliferation assays and analysis by mass spectrometry, cells were incubated for 1 h in 3% (wt/v) F68 in PBS at $7.2×10^6$ cells/mL and at $6×10^7$ cells/mL, respectively.

Device Fabrication and Use.

Digital microfluidic devices were fabricated using conventional microfabrication methods. 100 nm thick gold electrodes were patterned on the bottom plate of a device (glass wafer) and coated with 2 µm of Parylene-C and 50 nm of Teflon-AF. Unpatterned indium-tin oxide (ITO) coated glass substrates were coated with 50 nm of Teflon-AF. Devices were assembled with an unpatterned ITO-glass top plate and a patterned bottom plate and separated by a ~150 µm thick spacer. Driving potentials (100-140 $V_{RMS}$) were generated by amplifying the output of a function generator operating at 15 kHz. Droplets were sandwiched between the two plates and actuated by applying driving potentials between the top reference electrode 22 and sequential electrodes 14 on the bottom plate (FIG. 2(a)) via the exposed contact pads. Droplet actuation was monitored and recorded by a CCD camera mated to a stereomicroscope with fluorescence imaging capability. Most devices used here had a geometry identical to that shown in FIG. 2(a) (or FIG. 1), with 1 mm×1 mm actuation electrodes (suitable for manipulating 150 nL droplets), and inter-electrode gaps of 5-40 µm. The reservoirs were 2 mm×2 mm electrodes. Some devices had 7 mm×7 mm actuation electrodes which were used to manipulate much larger droplets (11 µL).

Electrical Field Modeling.

Figure 4:
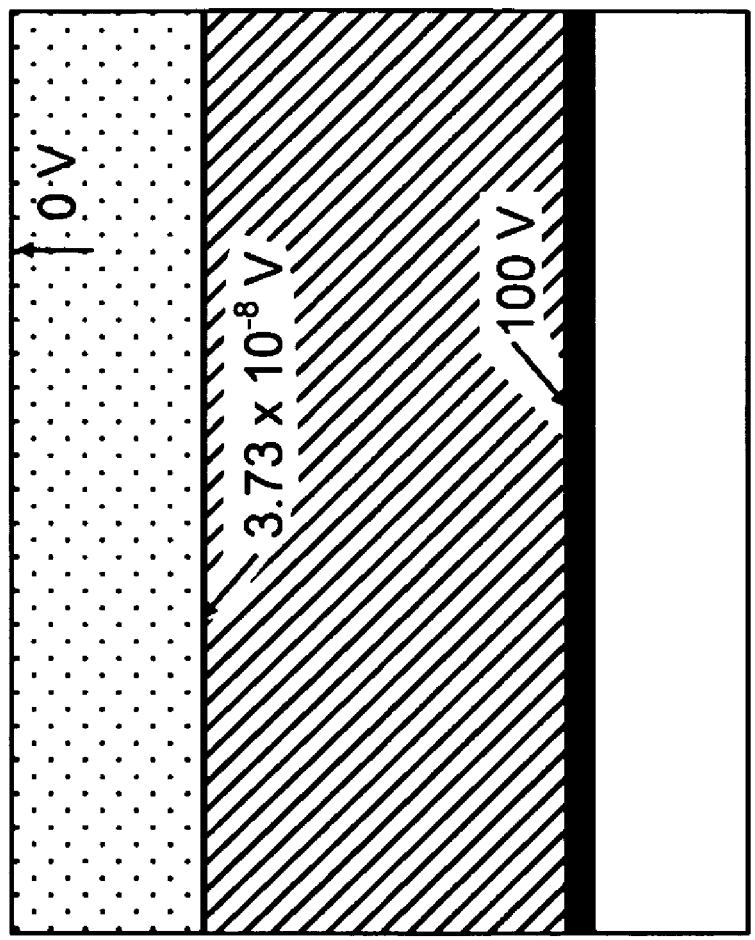
FIG. 4 is a plot of numerically simulated potential drops across a droplet and a dielectric layer.
Figure 4:
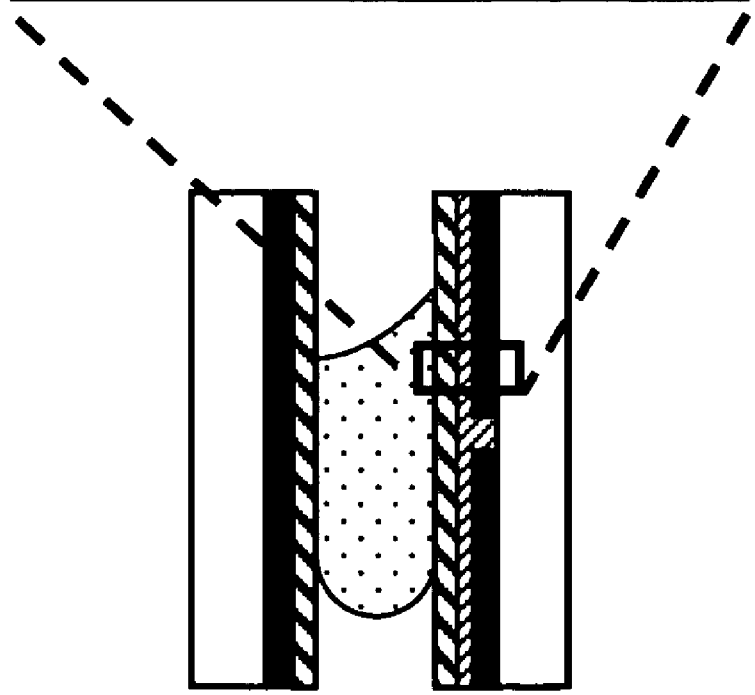

Electrical fields in digital microfluidic devices were modeled with COMSOL Multiphysics 3.3a (COMSOL, Burlington, Mass.) using the conductive media direct current module and the electrostatics module, shown in FIG. 4. The two-dimensional geometry of the model was nearly identical to the device illustrated in FIG. 2, including three patterned electrodes (1 mm length) on the bottom plate, a layer of Parylene-C (2 µm thick), a layer of PBS and air (150 µm thick), and a continuous electrode on the top plate. The hydrophobic Teflon AF layer 18 was omitted from the model because of its porosity and insignificant thickness. Dielectric constants, $\epsilon$, and conductivities, $\sigma$, used in the model included $\epsilon_{parylene}=2.65$, $\epsilon_{pbs}=70$, $\epsilon_{air}=1$, $\sigma_{parylene}=0$ S/m, $\sigma_{air}=0$ S/m, and $\sigma_{pbs}=4.7$ S/m (measured using a conductivity meter). With a 100 V potential applied between the bottom-right electrode and the top electrode (ground), a mesh with 233,831 triangular elements was used to simulate electrical field, using the linear solver UMFPACK.

Vitality Assays.

Figure 6B:
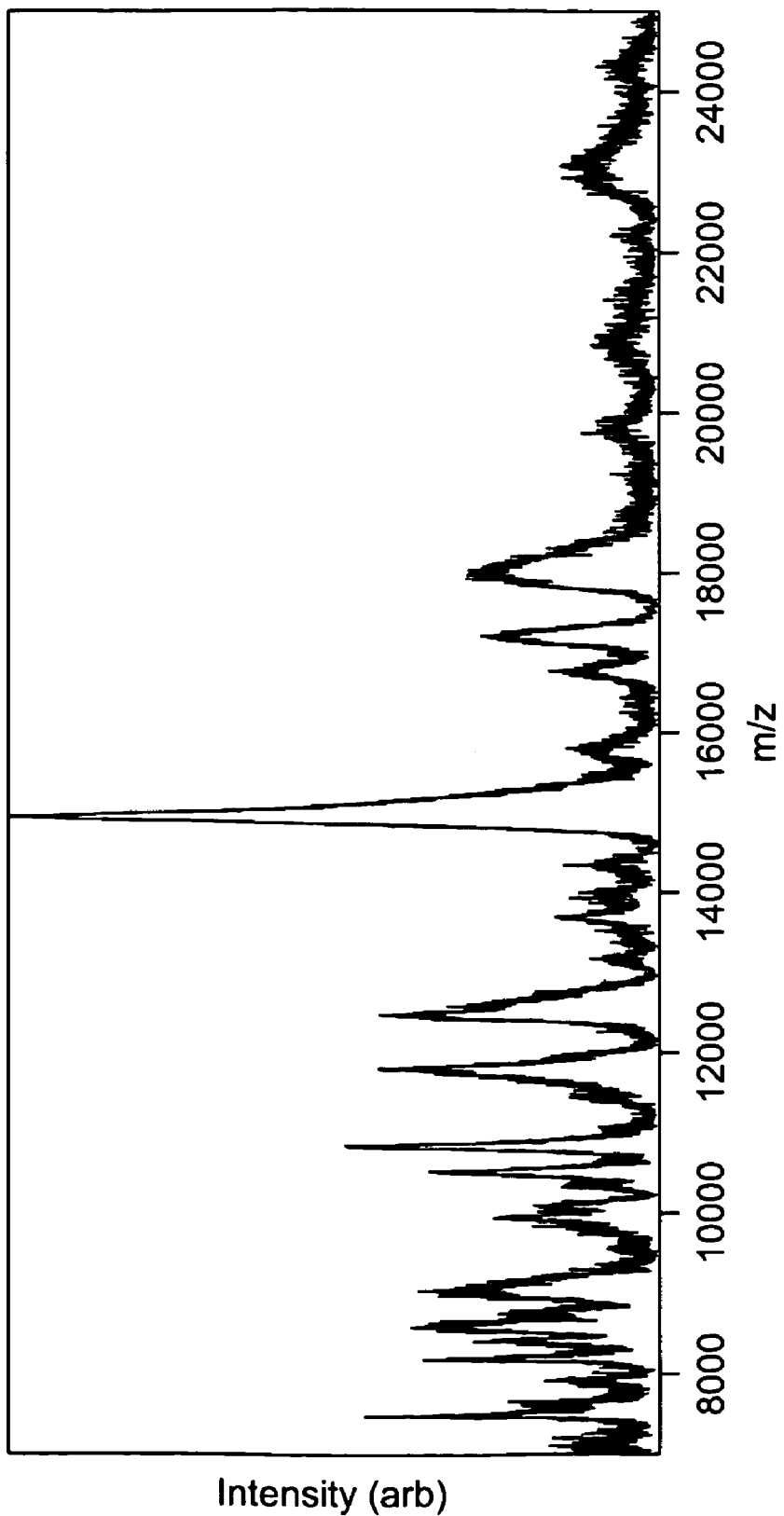

The effects of the electric field driven droplet actuation on cell vitality were evaluated by three assays, measuring cell viability (FIG. 5 day 0), proliferation (FIG. 5 day 2), and biochemistry (FIG. 6). In these vitality assays, large droplets (>1 µL) were used because the more conventional sub-microliter droplets (used in the cell phenotype assays) were difficult to handle off-chip and did not contain enough cells for analysis. In the cell viability and proliferation assays, ten 11 µL droplets of cells suspended in PBS/F68 (each containing ~79,200 cells) were actuated on devices with 7×7 mm electrodes. Each droplet was moved across 10 electrodes (approximately 15 s of actuation per droplet) and was then removed from the device and suspended in 300 µL of cell medium at $2.5 \times 10^5$ cells/mL. For viability assays, immediately after suspension in media, live and dead cells were counted on a hemacytometer with trypan blue exclusion. For proliferation assays, live and dead cells were counted after 48 h of incubation off-chip (humidified incubator, 5% $CO_2$, 37° C.). A second group of ten 11 µL droplets of the original cell solution (in PBS/F68) were treated identically, but were not actuated, and served as a control. The data was analyzed with two-tailed t-test assuming unequal variances.

In the cell biochemistry assay, four 11 µL droplets of cell suspension (~$6.6 \times 10^5$ cells/droplet) were actuated over ten electrodes as above, and were then pooled and suspended in lysing medium at $3 \times 10^7$ cells/mL. Lysing medium was PBS with 3% (wt/v) F68, 1% Triton X-100, and 1 mM phenylmethylsulphonyl fluoride (PMSF). After incubation on ice (30 min), the lysate was centrifuged (12,000 rpm, 5 min) and the supernatant was collected and stored in a −85° C. freezer. Immediately prior to analysis, the supernatant (100 µL) was thawed and desalted using a microspin G-25 column (Amersham BioSciences, Piscataway, N.J.) at 2800 rpm for 2 min. Proteins were eluted in distilled water with 0.05% (v/v) Kathon (1.5 µL), and the eluent was spotted onto a MALDI (matrix assisted laser desorption/ionization) target plate. A 1.5 µL aliquot of MALDI matrix solution (10 mg/mL sinapinic acid in 80% (v/v) acetonitrile/water) was added and the combined droplet was allowed to dry. Non-actuated droplets of the original cell suspension were lysed and processed identically, and served as a control.

Samples were analyzed using a MALDI-TOF Micro MX mass spectrometer (Waters, Milford, Mass.) in linear positive mode for the mass range of 4,000 to 25,000 m/z. One hundred shots were collected per spectrum, with laser power tuned to optimize the signal over noise ratio. Data were then processed by normalization to the largest analyte peak, baseline subtraction, smoothed with a 15-point running average.

Cell Phenotype Assays.

For phenotypic assays, cells were exposed to the surfactant, Tween 20 (lethal to mammalian cells at high concentrations), diluted in working buffer in a range of concentrations (0.002% to 0.5% (wt/vol)). Each Tween 20 concentration was evaluated in 4-6 replicates. In each experiment, a 150 nL droplet containing ~525 cells was dispensed and merged with a 150 nL droplet containing Tween 20. The merged droplets were then actively mixed by moving them on four neighboring electrodes in a circle. After 20 min of incubation in a humidified environment (a closed petri dish half-filled with water), the combined droplet containing cells and Tween 20 was merged and mixed with a 150-nL probe droplet containing viability dye(s), and then incubated for a second time in a humidified environment (20 min). In all experiments, the probe droplet contained calcein AM (1 µM in the working buffer), and in some experiments, the droplet also contained ethidium homodimer-1 (2 µM in the working buffer).

For quantitative experiments, a digital microfluidic device was positioned on the top of a well plate and inserted into a fluorescence microplate reader (Pherastar, BMG Labtech, Durham, N.C.) equipped with a module for 480 nm excitation and 520 nm emission. Each droplet was evaluated using a multipoint scanning program, in which the average fluorescence was recorded from each of 9 excitation flashes illuminated onto a 1-mm square 3×3 array with 0.5 mm resolution. The array was located in the centre of each droplet, and the focal height was set for each analysis at the highest-signal intensity, with gain=376. This multipoint program, designed by BMG Labtech for standard assays in well plates, was found empirically to have lower variance between runs than comparable single point analyses. Samples containing only Tween 20, pluronic F68, and calcein AM in PBS were evaluated to determine the background signal. Each analysis was repeated 4-6 times to determine standard deviations. All data were normalized to the average fluorescence intensity of cell samples exposed to control droplets (containing no Tween-20), and were plotted as a function of Tween-20 concentration.

For comparison, each assay implemented by digital microfluidics was duplicated in standard 384-well plates by pipetting reagents, cells, and dyes. In these experiments, all parameters were identical to those described above, except that the ~525 cells, reagents, and dyes were suspended in a final volume of 15 µL.

Culturing and Assaying Adherent Cells

The majority of mammalian cells are adherent, i.e. anchorage dependent. In a further embodiment of the present invention, we demonstrate that DMF can also be used to culture and assay adherent cells. In in vitro conditions, adherent cells grow in layers attached to a substrate that is typically hydrophilic and negatively charged, such as tissue culture treated polystyrene. Cells are maintained/grown in cell culture (growth) media in incubators with humidified atmosphere at 37° C. and with 5% $CO_2$.

As shown in FIGS. 11a, 11b, 11c, and 11d, the surface of a DMF device 200 (specifically the hydrophobic surface 18 that covers the dielectric material 16 on the lower electrode 14 (see FIG. 2(a)) is modified in specific areas, cell culture sites (CCS) 202, to facilitate cell adhesion and proliferation (cell growth and division). The surface modification procedure reported here makes use of standard techniques, such as depositing (microprinting, micorstamping) a bio-substrate (typically extracellular matrix proteins 206), rendering a hydrophilic and charged surface via microfabrication, or any other surface modification procedure that can also be cell specific.

In addition to using standard techniques, a bio-substrate can be formed by dispensing a droplet of a bio-substrate solution in a DMF device and translating it to the cell culture site 202, where after incubation and drying, it forms a bio-substrate layer for cell attachment. In this case, a device has an extra reservoir holding the bio-substrate solution. After the cell culture site 202 is formed, cells are seeded by generating a droplet 214 of growth media with suspended cells 212 on the cell culture site CCS 202 (FIG. 11c). Cells are allowed to adhere to the surface forming a cell monolayer 204 (FIG. 11d).

There are two ways of generating a droplet 214 on the cell culture sites 202: (1) by actively dispensing a droplet from a device reservoir or via external means (e.g. pipetting) and translating the droplet to the cell culture sites 202 (FIG. 11(a)), and (2) by actuating a droplet 216 (source droplet) larger than the cell culture sites 202 over the cell culture sites 202 and thereby passively dispensing the desired droplet on the hydrophilic cell culture sites 202 (FIG. 11(*b*)). Passive dispensing will be described in more details in the following section.

Passive Dipensing, Passive Washing, Passive Media/Reagent Exchange

Figure 12:
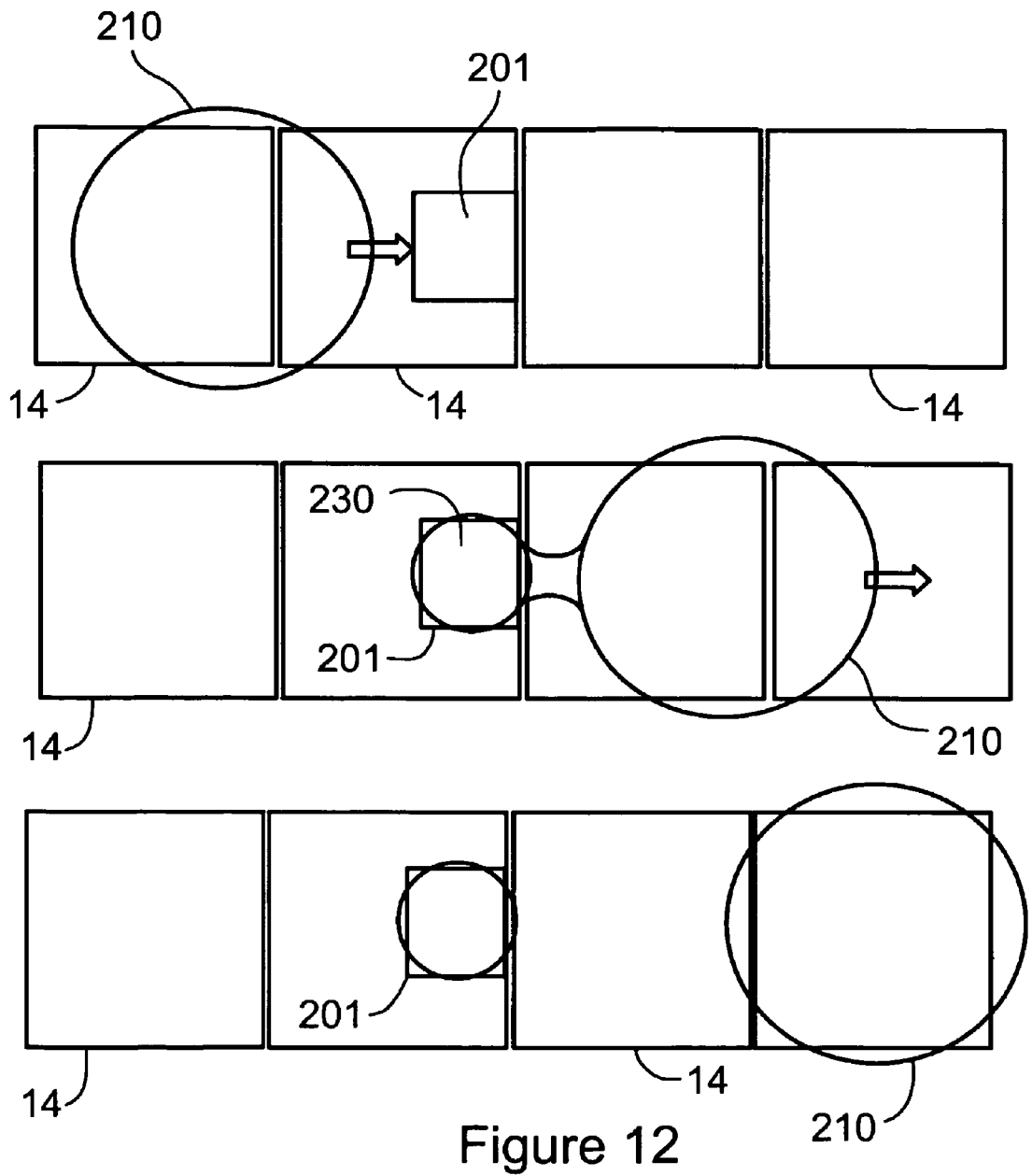
FIG. 12 is a diagrammatic representation showing passive dispensing of a droplet where a source droplet provides a smaller liquid droplet located on the CCS.

Referring to FIG. 12, when a source droplet 210 is actuated in a DMF device over a patterned hydrophilic area 201 smaller than the base area of the source droplet 210, it leaves behind a smaller droplet 230 on the hydrophilic area 201 and the rest of source droplet 210 is translated away from droplet 230. This method of generating droplets is termed passive dispensing. Methods for producing the hydrophilic areas 201 include but are not limited to microfabrication techniques (e.g. exposing hydrophilic layers of a device, such as glass or electrodes, in specific areas), hydrophobic surface plasma treatment, or deposition of a thin, patterned, hydrophilic layer onto a device surface. Hydrophilic areas can be formed on either the top plate, the bottom plate, or both the top and bottom plate of a two plate device. In the applications disclosed herein of adherent cell culture and assaying, hydrophilic areas 201 are used as the cell culturing sites (indicated by reference numeral 202 in FIG. 11) which preferably patterned by depositing bio-substrates, made from cell specific constituents, such as, but not limited to, extracellular matrix (ECM) proteins. ECMs are more favorable substrate for cell attachment than bare glass, electrodes, or a dielectric layer.

Examples of extracellular matrix proteins include, but are not limited to fibronectin, laminin, collagen, elastin. The cell specific constituents may also comprise synthetic molecules comprised of one of poly-L-lysine, poly-D-lysine and any combination thereof for example.

Typically, there are no electrodes underneath hydrophilic areas, as these areas (inherently hydrophilic) do not need to be electrically addressed to attract droplets; however, they have to be at least in the vicinity of electrodes. It will be appreciated that the hydrophilic arrays can also be formed on the top surface of the layer coating electrodes right above electrodes themselves. In most cell-based applications, it is desirable to have transparent attachment substrate to enable facile cell visualization.

Figure 13:
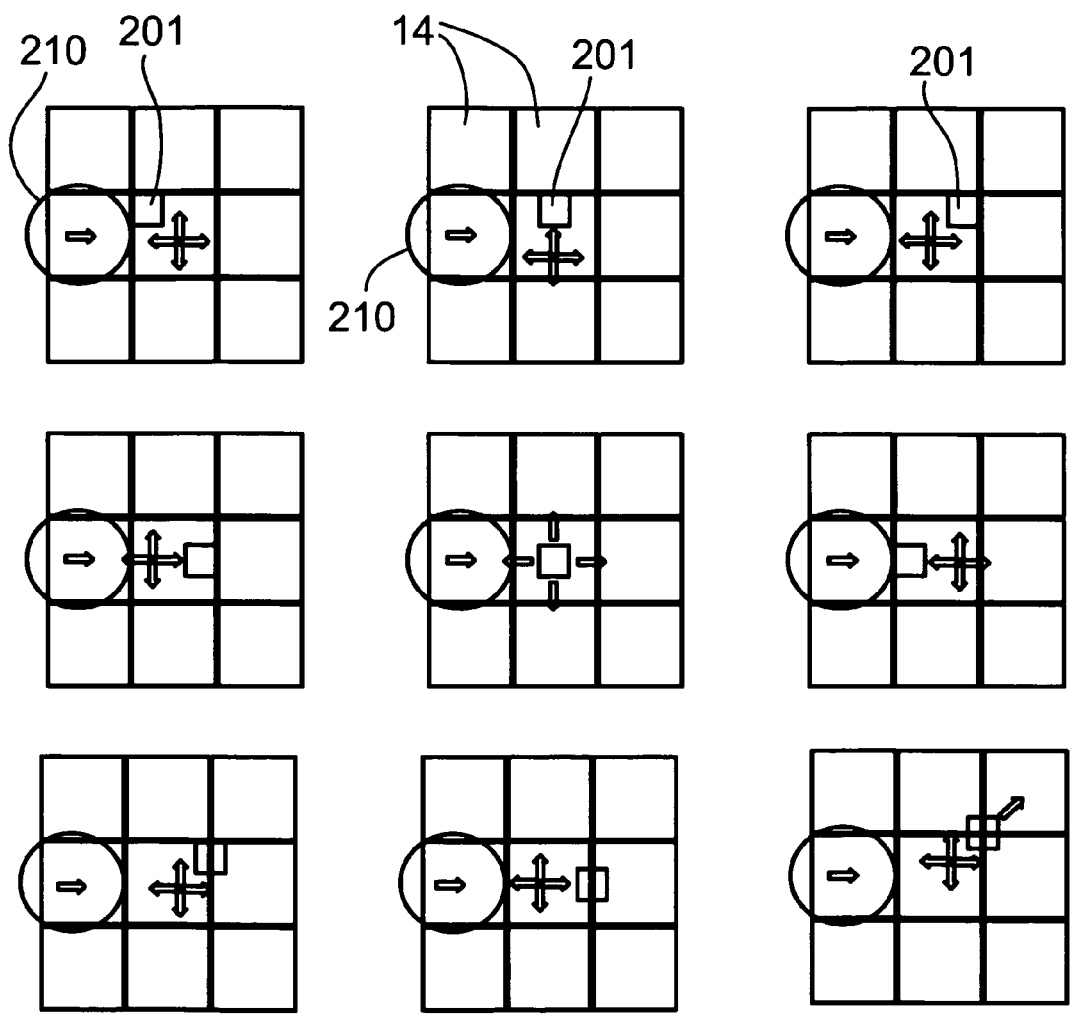
FIG. 13 shows several examples of the hydrophilic area positions relative to actuating electrodes and to the source droplet path.

Referring to FIG. 13, the size and position of a hydrophilic area can vary relative to size and position of electrodes 14 for source droplets actuation. Two relative sizes of hydrophilic areas—¼ and ⅑ of the electrode size were studied, and several positions relative to electrodes 14 and to a source droplet path. It should be noted that size and position of hydrophilic areas 201 is not limited by the examples in FIG. 13, and that the shape of hydrophilic areas 201 and actuating electrodes 14 is not limited to the square shape.

Figure 14:
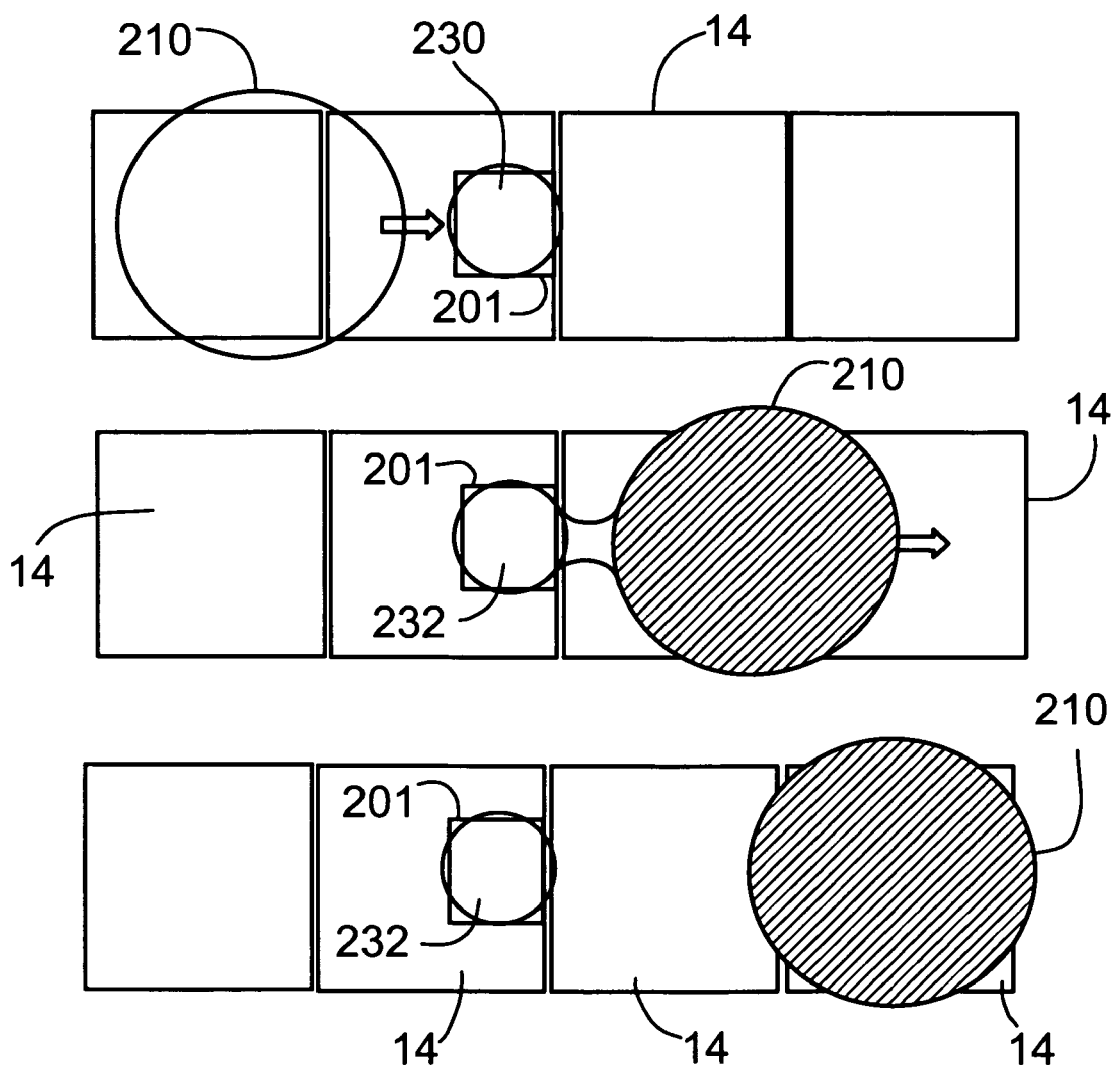
FIG. 14 shows a diagrammatic representation showing a passive washing/exchange process whereby a droplet on a CCS is replaced by a new droplet.
Figure 15:
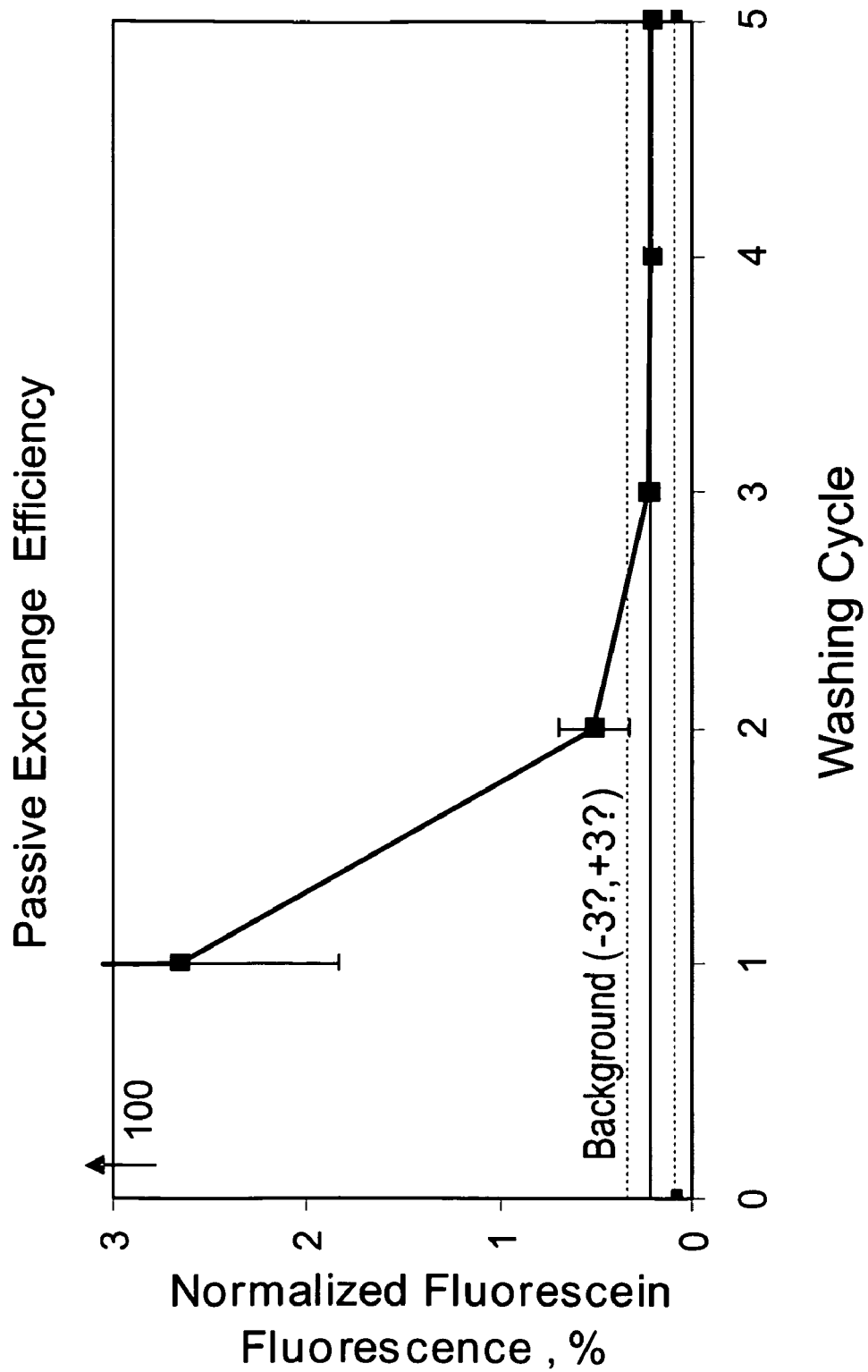
FIG. 15 shows a graph of fluorescein fluorescence signal intensity versus washing cycle to show washing efficiency.

Referring to FIG. 14, when a hydrophilic area 201 is already occupied by a droplet 230, a source droplet 210 will remove the smaller droplet 230 and replace it with a new droplet 232 of the source solution while removing droplet 230 in droplet 210'. This process is termed passive washing or passive exchange of liquid solutions on hydrophilic areas 201 (e.g., on CCSs) in a DMF device. We report passive exchange efficiency of ≧95% with a single source droplet, or ≧99% with two or more consecutive source droplets. FIG. 15 shows efficency of 0.5 nM fluorescein passive exchange with phosphate buffered saline. These results were obtained with fibronectin hydrophilic areas 201, ~⅑ of the electrode size, having two different positions relative to actuating electrodes 14.

Culturing and Passaging Adherent Cells

Figure 16:
FIG. 16 shows a digital image of ~130 mouse fibroblast cells (NIH-3T3) cultured in a DMF device for 72 h; media was replenished using passive dispensing/exchange technique every 24 h; after 72 h cells were stained with calcein AM for viability.
Figure 17A:
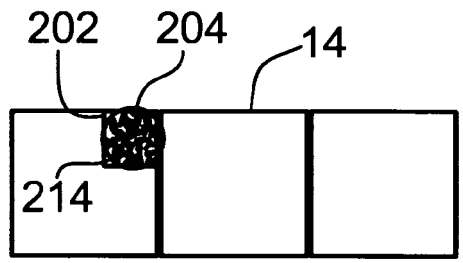
FIGS. 17(a) to (f) are diagrammatic representations of subculturing adherent cells in a DMF device in which (a) shows monolayer of adherent cells cultured on a CCS, (b) washing cells via passive exchange, (c) delivering a dissociation agent to cells via passive exchange, (d) detachment of cells after incubation with a dissociation agent, (e) blocking of a dissociation agent and resuspending cells via passive exchange, and (f) seeding of cells resuspended in fresh media on a new CCS.
Figure 17D:
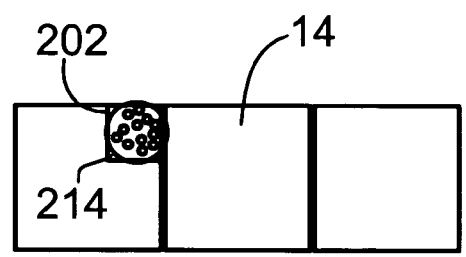
Figure 17B:
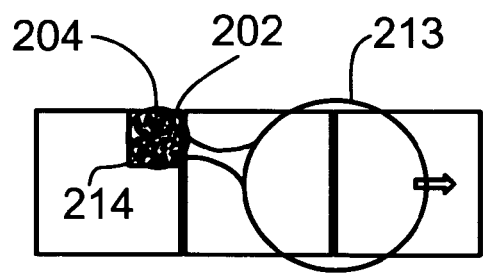
Figure 17E:
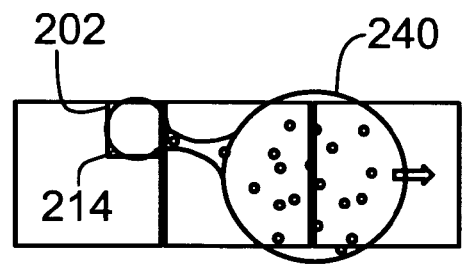
Figure 17C:
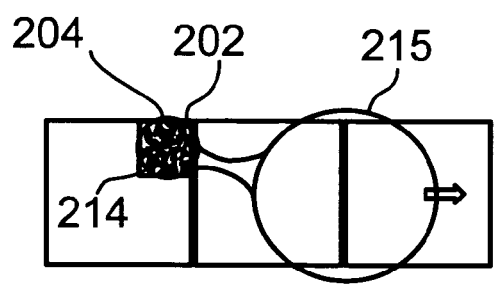
Figure 17F:
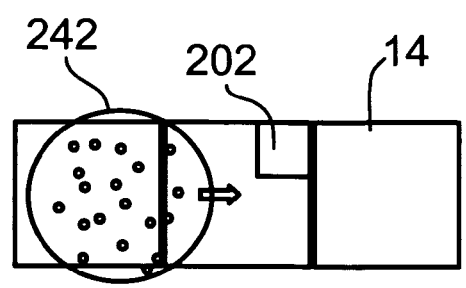

For adherent cell culture, a DMF device with seeded cells is placed in a cell culture incubator and a droplet of culture media on top of the cell layer 204 is regularly replenished with fresh media via DMF passive exchange every 24 h. We report culturing cells on cell culture sites 202 for 72 h; growth characteristics and morphology of the cells are comparable to cells grown in standard tissue culture flasks (FIG. 16). No detachment of cells was observed during media droplet actuation over the cell culture sites 202. Cells are subcultured at regular intervals using standard subculturing protocols adapted to DMF system: (1) washing cells as shown in FIG. 17(*b*) in which washing droplet 213 has been dispensed and translated over cell culture site 202, (2) harvesting cells by dispensing and translating a droplet 215 containing a dissociation agent (e.g. trypsin, collagenase) over cell culture site 202 as shown in FIG. 17(*c*) and incubating to detach the adhered cells and resuspend them as shown in FIG. 17(*d*), (3) a droplet 240 containing a blocking agent (typically serum in cell culture media) for blocking the dissociation agent is dispensed and translated over cell culture site 202, while removing the detached cells away from the cell culture sites 202 as shown in FIG. 17(*e*), (4) splitting the resulting cell suspension as necessary and resuspending in fresh media in droplet 242 and (5) seeding resuspended cells on a new cell culture site 202 as shown in FIG. 17(*f*). Blocked dissociation agent and cell suspension are diluted in a big source droplet 240 of a blocking agent (cell culture media with serum) by the ratio of the volumes of the two droplets, cell culture site 202 droplet and the source droplet. In step (4), the resulting cell suspension can be split in smaller droplets and resuspended in droplets of fresh media for further reduction of cell concentration. When a desired cell concentration is achieved, new generation of cells is seeded on new cell culture sites 202 by either translating actively dispensed droplets of the cell suspension to new cell culture sites, or by passively dispensing droplets with cells on cell culture sites 202 from droplet 242 (FIG. 17*f*). The inventors have demonstrated subculturing several generations of mammalian cells in the same DMF device following the procedure outlined above.

Assaying Adherent Cells

Adherent cell assays in DMF devices are executed in droplets on cell culture sites 202 where adherent cells are seeded. Devices with seeded cells are placed in incubators for few hours or overnight to allow cell attachment and adjustment to a new DMF device environment (FIG. 18*a*). When adherent cell deposits 204 are ready for assaying, droplets of reagents and washing solutions are deposited on cell culture sites 202 either by translating a droplet actively dispensed from a device reservoir or externally, or by passive dispensing/exchange from source droplets 250 (FIG. 18*b*). Source droplets 250 are either dispensed via DMF from reservoirs or externally deposited on a device. Washing solutions and reagents are incubated with cells following cell assay protocols (FIG. 18*c*). Upon assay completion, cell response to a stimulus (e.g. a lead drug compound) can be detected and measured by apparatus 260 which may be any standard means (e.g. fluorescence microscopy, microplate reader to give a few examples) (FIG. 18*d*).

In assays targeting extracellular biochemistry (growth factors, signaling molecules, metabolic products, etc.), cell response to stimulus is detected in medium where cells are grown and stimulated with reagents, rather than in cells. Medium can be analyzed by immunoassays or other means. Droplets of cell suspension can alternatively be removed from the cell culture sites 202 (e.g. with a bigger source droplet) and its signal can be detected on another spot or its contents can be analyzed externally.

Multiplexed Adherent Cell Culture/Cell Assays

Figure 19:
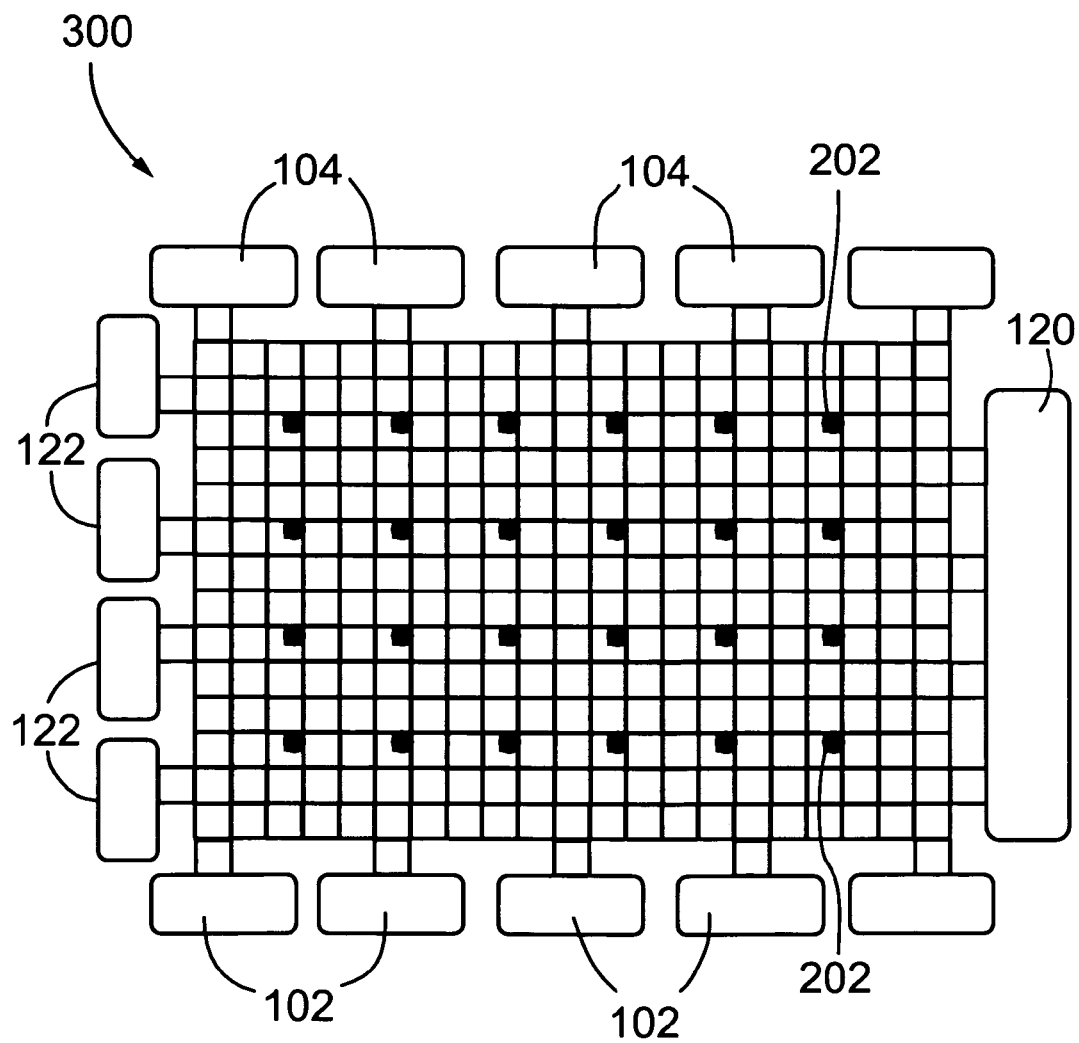
FIG. 19 shows a DMF device for multiplexed cell assays with adherent cells using passive dispensing and passive reagent exchange.

Referring to FIG. 19, multiple cell culturing sites 202 in a DMF device 300 which is similar to device 100 in FIG. 10 but device 300 includes a plurality of cell culture sites 202. Device 300 may be used in multiplexed assays where cells of one kind or multiple kinds are assayed with one or multiple reagents simultaneously in which cell culturing may be involved as well. In addition, a single cell culture site 202 can be seeded with multiple cell lines (cell co-culture). Assay reagents and/or culture media can be delivered to cell culture sites 202 via passive dispensing/exchange or in actively dispensed droplets.

In a multiplexed assay, a single source droplet can deliver reagents to multiple cell culture sites 202 (serial passive dispensing/exchange), or to only one cell culture site 202 (parallel passive dispensing/exchange). Signals from assayed cells or suspension media is detected using multiplexed detection instruments such as microplate readers.

Experimental

The following non-limiting examples demonstrates the efficacy of the present invention for conducting adherent cell assays and culture.

Device Design and Fabrication.

Digital microfluidic devices were fabricated using conventional microfabrication methods. 100 nm thick gold electrodes were patterned on the bottom plate of a device (glass wafer) and coated with 2 μm of Parylene-C and 50 nm of Teflon-AF. Unpatterned indium-tin oxide (ITO) coated glass substrates were coated with 50 nm of Teflon-AF. Devices were assembled with an unpatterned ITO-glass top plate and a patterned bottom plate and separated by a ~150 μm thick spacer. Driving potentials (100-140 $V_{RMS}$) were generated by amplifying the output of a function generator operating at 15 kHz. Droplets were sandwiched between the two plates and actuated by applying driving potentials between the top reference electrode 22 and sequential electrodes 14 on the bottom plate (FIG. 2(a)) via the exposed contact pads. Most devices had a basic geometry identical to that shown in FIG. 11 with the addition of reservoirs. Source droplets (~800 nL) were actuated on 2.5 mm×2.5 mm actuation electrodes, and smaller droplets were actuated on 0.8 mm×0.8 mm actuation electrodes. Cell culture site (CCS) areas were patterned either as transparent, non-conductive fields in 2.5 mm×2.5 mm electrodes or as smaller (0.8 mm×0.8 mm) electrodes within the area of larger 2.5 mm×2.5 mm electrodes. Devices were sterilized in 70% ethanol prior to use.

Cell Culture

NIH-3T3 cells (mouse fibroblasts) were maintained in a humidified atmosphere (5% $CO_2$, 37° C.) in DMEM supplemented with 10% fetal bovine serum, penicillin (100 IU $mL^{-1}$), and streptomycin (100 μg $mL^{-1}$). Cells were subcultured every 2-3 days at $5\times10^3$ cells $cm.^{-2}$ Prior to each DMF experiment, cells were suspended in DMEM with the addition of 0.05% (wt/v) pluronic F68 (Sigma-Aldrich) at ~$7\times10^5$ cells $mL.^{-1}$ Cell number and viability were quantified using a hemocytometer and trypan blue exclusion (Invitrogen Canada) immediately prior to all experiments.

DMF Cell Seeding

CCSs were formed by depositing 500 nL droplets of fibronectin (100 μg $mL^{-1}$ in $ddH_2O$) on designated areas in DMF devices. Fibronectin solution was air-dried resulting in ~1 $mm^2$ bio-substrates with ~5 μg/$cm^2$ of fibronectin. Cell suspension was delivered to CCSs by either passive dispensing from a source droplet or by translating actively dispensed droplets from a device reservoir to CCSs. CCS droplets were ~200 nL in volume and contained ~140 cells. Cells were allowed to attach to the substrate and adapt overnight in a cell culture incubator (5% $CO_2$, 37° C.).

DMF Cell Culture

NIH-3T3 cells were maintained on CCSs by changing media via passive dispensing every 24 hours. Complete DMEM containing 0.05% (wt/v) pluronic F68 was dispensed in ~800 nL droplets and translated over CCSs while replenishing CCS droplet of media. Complete media exchange was accomplished with two consecutive source droplets and cells were returned to the incubator. No cell detachment was observed during passive media exchange.

DMF Cell Subculture

Upon reaching confluency on CCSs, cells were subcultured following standard subculturing protocols adapted to the DMF format. All reagents and media containing 0.05% (wt/v) pluronic F68 were delivered to cells using passive dispensing/exchange from two consecutive source droplets. Cells were first washed with PBS without $Ca^{2+}/Mg^{2+}$ and then supplied and incubated with GIBCO Trypsin-EDTA dissociation agent (0.25% Trypsin, 1 mM EDTA 4Na) for 5-10 min at 37° C. DMEM source droplet was then translated to the CCS to block the dissociation agent with the serum present in media, whereby harvested cells were resuspended in DMEM droplet at the 1:4 ratio. DMEM droplet with suspended cells was actuated away from the CCS and used either as a source droplet or a reservoir droplet to seed the new generation of cells on a new CCS in the same device. Seeded cells were placed in a cell culture incubator overnight followed by media change. Cells were grown on the new CCS for 2 days and further subcultured on the same device.

DMF Cell Viability Assay

Cells cultured on CCSs were assayed on a device for viability. Source droplets of 0.05% (wt/v) pluronic F68 (Sigma-Aldrich) in phosphate buffered saline containing viability dyes, calcein AM (1 μ) and ethidium homodimer-1 (2 μM) (Invitrogen Canada), were dispensed in a device and translated over the CCS. With two consecutive source droplets, growth media was removed from the CCS and replaced with viability dyes. Cells were incubated with dyes at room temperature and visualized using stereomicroscope. Viability of cells was higher than 95% and there was no significant difference in morphology between cells grown on CCSs and cells grown in cell culture flasks.

It will be understood that when doing cell culturing or cell assaying, the suspension of cells may contain a combination of cells, a suspension medium, and a non-ionic surfactant. The suspension medium may be selected to facilitate cell-containing droplet actuation by preventing non-specific adsorption of cells and proteins to device surfaces. The suspension of cells may be a combination of cells and a suspension medium comprised of block copolymers formed from poly(propylene oxide) and poly(ethylene oxide), pluronic F68, pluronic F127, hydrophilic polymers, sodium bicarbonate, phosphate buffered saline (PBS), HEPES, and other biological buffers, and any combination thereof, which may be combined or mixed with cell culture medium which in turn may include balanced salt solutions, nutrient mixtures, basal media, complex media, serum free media, insect cell media, virus production media, serum, fetal bovine serum, serum replacements, antibiotics, antimycotics, and any combination thereof.

In an embodiment the suspension of cells may be a combination of cells, phosphate buffered saline, and pluronic F68. The droplets including a cell assay reagent may include chemicals, biochemicals, drugs, drug lead compounds, toxins, surfactants, transfection reagents, supplements, cell culture media, anti-clumping agents, streptavidin, biotin, antibody production enhancers, antibodies, antibody ligands, nucleic acids, nucleic acid binding molecules, enzymes, proteins, viruses, cell process agonists or antagonists, labeling agents, fluorescent dyes, fluorogenic dyes, viability dyes, calcein AM, quantum dots, nano particles, Tween 20, and ethidium homodimer-1, block copolymers formed from poly (propylene oxide) and poly(ethylene oxide), pluronic F68, pluronic F127, hydrophilic polymers, sodium bicarbonate, phosphate buffered saline (PBS), HEPES, and other biological buffers, and any combination thereof, which may be combined or mixed with cell culture medium which in turn may include balanced salt solutions, nutrient mixtures, basal media, complex media, serum free media, insect cell media, virus production media, serum, fetal bovine serum, serum replacements, antibiotics, antimycotics, and any combination thereof.

The cells in the suspension of cells may include primary/isolated or transformed/cultured cells selected from the group consisting of various eukaryotic and prokaryotic cells, including animal cells (blood cells, human leukemia cells, lymphocytes, beta cells, oocytes, eggs, primary cells, primary bone marrow cells, stem cells, neuronal cells, endothelial cells, epithelial cells, fibroblasts), insect cells, plant cells, bacterial cells, archebacterial cells.

As used herein the word "incubation" can mean allowing a reaction to take place over a period of time under specified conditions. For cell assays involving mixing of cells with one or more cell assay reagents, the incubation period may be very short or almost instantaneous upon mixing the droplets wherein the reaction or response of the cells to the reagent occurs quickly. For cell culture, "incubation" can mean maintaining the cells growing or alive under specific conditions and the period of time of the "incubation" may be arbitrary, after which point the cells may be subcultured, assayed or subject to further culturing.

The results disclose herein demonstrate the utility of the present invention for its application of digital microfluidics to multiplexed, high throughput, phenotypic cell-based assays, an important tool used in drug discovery and environmental monitoring. To facilitate high-throughput screening, arrays of DMF cell culture sites (FIG. 19) can be addressed with compounds from chemical libraries, and the potential drugs evaluated on the basis of observed phenotypic changes. The proposed method will enable high-throughput phenotypic screening with 100-1000× lower reagent consumption than conventional methods; in addition, the devices are inexpensive (relative to robotic dispensers), have small laboratory footprint and no moving parts. This method could transform high-throughput screening, making it attractive to pharmaceutical companies and accessible for basic and applied scientists, world-wide.

In addition to cell assaying the inventors disclose herein the first multigenerational lab-on-a-chip cell culture using DMF devices. Cells are grown, maintained and subcultured in nanoliter volumes. DMF devices are inherently easily automated and as such have a high potential to be used as tool for a completely automated microscale cell culture system.

As used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

References (1) Verkman, A. S., "Drug discovery in academia," *American Journal of Physiology-Cell Physiology* 2004, 286, C465-C474.
(2) El-Ali, J., Sorger, P. K., Jensen, K. F., "Cells on chips," *Nature* 2006, 442, 403-411.
(3) Unger, M. A., Chou, H. P., Thorsen, T., Scherer, A., Quake, S. R., "Monolithic Microfabricated Valves and Pumps by Multilayer Soft Lithography," *Science* 2000, 288, 113-116.
(4) Yu, H. M., Alexander, C. M., Beebe, D. J., "A plate reader-compatible microchannel array for cell biology assays," *Lab on a Chip* 2007, 7, 388-391.
(5) Le Pesant, J.-P., 1987, U.S. Pat. No. 4,636,785.
(6) Ohkawa, T., 1996, U.S. Pat. No. 5,486,337.
(7) Washizu, M., Kurosawa, O., 1998, Japan 10267801.
(8) Washizu, M., "Electrostatic Actuation of Liquid Droplets for Microreactor Applications," *IEEE Transactions on Industry Applications* 1998, 34, 732-737.
(9) Lee, J., Moon, H., Fowler, J., Schoelihammer, T., Kim, C.-J., "Electrowetting and electrowetting-on-dielectric for microscale liquid handling," *Sensors & Actuators A* 2002, 95, 259-268.
(10) Pollack, M. G., Fair, R. B., Shenderov, A. D., "Electrowetting-based actuation of liquid droplets for microfluidic applications," *Applied Physics Letters* 2000, 77, 1725-1726.
(11) Shenderov, A. D., 2003, U.S. Pat. No. 6,565,727.
(12) Shenderov, A. D., 2007, U.S. Pat. No. 7,255,780.
(13) Elrod, S. A., Peeters, E. T., Biegelsen, D. K., Dunec, J. L., 2006, U.S. Pat. No. 7,147,763.
(14) Pamula, V. K., Pollack, M. G., Paik, P., H., R., Fair, R., 2005, U.S. Pat. No. 6,911,132.
(15) Chen, T.-H., Su, C.-M., Shih, H.-C., Yang, C.-T., "*Selective Wettability Assisted Nanoliter Sample Generation via Electrowetting-Based Transportation,*" Proceedings of the Fifth International Conference on Nanochannels, Microchannels and Minichannels (ICNMM2007), Puebla, Mexico, Jun. 18-20 2007.
(16) Pollack, M., G., Pamula, V., K., Srinivasan, V., Paik, P., Y., Eckhardt, A., E., Fair, R., B., 2007 WO/2007/120241.
(17) Huh, N., Lee, J.-g., 2007, US 20070148763
(18) Fan, S.-K., Huang, P.-W., Wang, T.-T., Peng, Y.-H., "Cross-scale electric manipulations of cells and droplets by frequency-modulated dielectrophoresis and electrowetting," *Lab on a Chip* 2008, 10.1039/b803204a.
(19) Smith, C. M., Hebbel, R. P., Tukey, D. P., Clawson, C. C., White, J. G., Vercellotti, G. M., "Pluronic F-68 Reduces the Endothelial Adherence and Improves the Rheology of Liganded Sickle Erythrocytes," *Blood* 1987, 69, 1631-1636.
(20) Mizrahi, A., "Pluronic Polyols in Human Lymphocyte Cell Line Cultures," *Journal of Clinical Microbiology* 1975, 2, 11-13.
(21) "Hyclone Media: CHO Cell Culture Plafform Media," http://www.hyclone.com/media/cho.htm, accessed in 2007.
(22) Thiede, B., Siejak, F., Dimmler, C., Jungblut, P. R., Rudel, T., "A two dimensional electrophoresis database of a human Jurkat T-cell line," *Electrophoresis* 2000, 21, 2713-2720.

Therefore what is claimed is:

1. A method of performing droplet-based cell culture, comprising the steps of:
 a) providing a digital microfluidic device comprising:
  an array of actuating electrodes formed on a substrate surface; and
  a coating formed on the substrate surface, the coating providing a working surface;

wherein said actuating electrodes are connectable to an actuating electrode controller for exciting or de-exciting the actuating electrodes for translating liquid droplets over the working surface;
b) providing a cell-containing droplet at a location on the working surface, the cell-containing droplet containing cells and cell culture medium;
c) incubating the digital microfluidic device in a controlled environment to culture the cells;
d) actuating electrodes of the array to dispense a droplet containing cell culture media to the cell-containing droplet; and
e) incubating the digital microfluidic device in the controlled environment to further culture the cells.

2. The method according to claim 1, wherein steps d) and e) are performed one or more additional times.

3. The method according to claim 1, wherein step d) further comprises actuating electrodes of the array and splitting the cell containing droplet into at least two smaller cell-containing droplets.

4. The method according to claim 3, wherein step d) is repeated one or more times.

5. The method according to claim 4 wherein step d) is performed a sufficient number of times to generate at least one smaller cell-containing droplet containing a single cell.

6. The method according to claim 1, wherein the cells include adherent cells, and wherein the location in step b) includes a cell culture site adapted for adhesion and proliferation of adherent cells, such that the adherent cells adhere to the cell culture site during steps c) to e).

7. The method according to claim 6, wherein step b) includes:
actuating electrodes of the array to transport one or more droplets containing adherent cells and cell culture media to the location on the working surface, thereby providing the cell-containing droplet at the location on the working surface, such that the adherent cells adhere to the cell culture site.

8. The method according to claim 7, wherein actuating electrodes of the array to transport one or more droplets containing adherent cells and cell culture media to the location on the working surface includes actuating electrodes of the array to dispense a cell-containing droplet larger than the cell culture site over the cell culture site, thereby passively dispensing a smaller cell-containing droplet on the cell culture site.

9. The method according to claim 6, wherein in step d), the droplet containing cell culture medium is dispensed to the cell-containing droplet such that the droplet on the cell culture site is replaced by at least a portion of the droplet containing cell culture media, such that the adherent cells attached to the cell culture site are submersed in the cell culture medium.

10. The method according to claim 9, wherein steps d) and are performed one or more additional times.

11. The method according to claim 9 further comprising performing one or more cell assays on the adherent cells after culturing the adherent cells.

12. The method according to claim 11, wherein performing the one or more cell assays on the adherent cells after culturing the adherent cells includes detecting signals emitted from the cell containing droplet using a device capable of detecting a signal from a cell-containing droplet selected from the group consisting of optical sensors, optical detectors comprising a light source and a photodetector, optical detectors that measure any one or combination of absorbance, fluorescence, epifluorescence, and chemiluminescence, UV light detectors, radiometric detectors, any one of scanning, imaging, and confocal microscopy detectors, CCD cameras, and microplate readers.

13. The method according to claim 11, wherein performing one or more assays includes actuating electrodes of the array to dispense one or more assay reagents to the adherent cells.

14. The method according to claim 9, wherein in step d), the droplet containing cell culture media has a base area larger than the cell culture site, and wherein after actuating electrodes of the array to dispense the droplet containing cell culture media to the cell-containing droplet, the method further comprises actuating electrodes of the array to remove a droplet from a region including the cell culture site, such that a smaller droplet containing cell culture media remains behind on the cell culture site.

15. The method according to claim 14, wherein steps d) and e) are performed one or more additional times.

16. The method according to claim 14 wherein the cell culture site is hydrophillic.

17. The method according to claim 9 further comprising:
translating one or more droplets containing a washing solution over one or more cell culture sites;
dispensing one or more droplets containing a cell dissociation agent to the cell culture sites; and
incubating the digital microfluidic device for a time duration sufficient to detach the adherent cells from the cell culture site, thereby forming a droplet containing resuspended cells.

18. The method according to claim 17 further comprising dispensing one or more additional droplets to said droplet containing resuspended cells, wherein said one or more additional droplets contain cell culture media.

19. The method according to claim 6, wherein the cell culture site is prepared by depositing a bio-substrate on the working surface.

20. The method according to claim 19, wherein said bio-substrate is deposited using any one of microprinting and microstamping.

21. The method according to claim 19, wherein said bio-substrate is produced from cell specific constituents.

22. The method according to claim 21, wherein said cell specific constituents are extracellular matrix proteins.

23. The method according to claim 22, wherein said extracellular matrix proteins include any one of fibronectin, laminin, collagen, elastin and any combination thereof.

24. The method according to claim 21, wherein said cell specific constituents are synthetic molecules comprised of one of poly-L-lysine, poly-D-lysine and any combination thereof.

25. The method according to claim 6, wherein the coating includes any one of a hydrophobic layer and a dielectric layer, and wherein the cell culture site is prepared using any one or combination of plasma treatment, hydrophobic layer etching, dielectric layer etching, electrode etching and stamping.

26. The method according to claim 6 wherein the cell culture site is hydrophillic.

27. The method according to claim 1, wherein step b) is performed by actuating electrodes of the array to transport one or more cell-containing droplet and droplet containing cell culture medium to the location on the working surface.

28. The method according to claim 1, wherein step b) is performed by transporting one or more droplets from one or more sources external to said digital microfluidic device.

29. The method according to claim 28, wherein the one or more sources external to said digital microfluidic device are selected from the group consisting of pipettes, robotic dispensers, microprinters and microstamps.

30. The method according to claim 1, wherein step b) is performed by dispensing one or more droplets containing cells and cell culture media from one or more sources integrated as part of said digital microfluidic device, said one or more sources being in flow communication with said working surface.

31. The method according to claim 30, wherein the one or more sources integrated as part of said digital microfluidic device are liquid reservoirs.

32. The method according to claim 31, wherein the liquid reservoirs are formed on said working surface above some of said actuating electrodes which are modified to act as said liquid reservoirs.

33. The method according to claim 1, wherein step b) is performed by dispensing one or more droplets containing cells and cell culture media from one or more sources integrated as part of a cartridge assembled with said digital microfluidic device, said one or more sources being in flow communication with said working surface.

34. The method according to claim 1, wherein the cell-containing droplet is a combination of cells, a suspension medium, and a non-ionic surfactant.

35. The method according to claim 34, wherein said suspension medium is selected to facilitate cell-containing droplet actuation by preventing non-specific adsorption of cells and proteins to device surfaces.

36. The method according to claim 34, wherein the cell-containing droplet is a combination of cells and a suspension medium selected from the group consisting of block copolymers formed from poly(propylene oxide) and poly(ethylene oxide), poloxamer 188, poloxamer 407, hydrophilic polymers, sodium bicarbonate, phosphate buffered saline (PBS), HEPES, and cell culture medium selected from the group consisting of balanced salt solutions, nutrient mixtures, basal media, complex media, serum free media, insect cell media, virus production media, serum, fetal bovine serum, serum replacements, antibiotics, antimycotics, and any combination thereof.

37. The method according to claim 34, wherein the cell-containing droplet is a combination of cells, phosphate buffered saline, and poloxamer 188.

38. The method according to claim 1, further comprising actuating electrodes of the array to dispense at least one additional droplet to the cell-containing droplet, wherein the additional droplet contains a substance selected from the group consisting of chemicals, biochemicals, drugs, drug lead compounds, toxins, surfactants, transfection reagents, supplements, anti-clumping agents, streptavidin, biotin, antibody production enhancers, antibodies, antibody ligands, nucleic acids, nucleic acid binding molecules, enzymes, proteins, viruses, cell process agonists or antagonists, labeling agents, fluorescent dyes, fluorogenic dyes, viability dyes, calcein AM, quantum dots, nano particles, polysorbate 20, ethidium homodimer-1, block copolymers formed from poly(propylene oxide) and poly(ethylene oxide), poloxamer 188, poloxamer 407, hydrophilic polymers, sodium bicarbonate, phosphate buffered saline (PBS), HEPES, and cell culture medium selected from the group consisting of balanced salt solutions, nutrient mixtures, basal media, complex media, serum free media, insect cell media, virus production media, serum, fetal bovine serum, serum replacements, antibiotics, antimycotics, and any combination thereof.

39. The method according to claim 1, wherein the cells include primary/isolated or transformed/cultured cells selected from the group consisting of prokaryotic cells, eukaryotic cells, animal cells, blood cells, human leukemia cells, lymphocytes, beta cells, oocytes, eggs, primary cells, primary bone marrow cells, stem cells, neuronal cells, endothelial cells, epithelial cells, fibroblasts, insect cells, plant cells, bacterial cells, and archaebacterial cells.

40. The method according to claim 1, wherein the cell containing droplet has a cell density less than about $1 \times 10^3$ cells/mL.

41. The method according to claim 1 conducted in a substantially sterile chamber.

42. The method according to claim 41 further comprising translating at least some cells mixed with the cell culture media to at least one new cell culture site to seed a new generation of cells.

43. The method according to claim 1, wherein the environment is controlled by regulating conditions including humidity, temperature and atmosphere.

44. The method according to claim 1 performed in a multiplexed mode, wherein:
said step b) of providing a cell-containing droplet at a location on the working surface includes providing a plurality of cell-containing droplets at a plurality of locations on the working surface, each cell-containing droplet containing cells and cell culture media; and
wherein said step d) of actuating electrodes of the array to dispense a droplet containing cell culture media to the cell-containing droplet includes actuating electrodes of the array to dispense a plurality of droplets, containing cell culture media to the cell-containing droplets such that at least one droplet containing cell culture media is dispensed to each cell-containing droplet.

45. The method according to claim 44, wherein the plurality of droplets containing cell culture medium is equal in number to the plurality of cell-containing droplets.

46. The method according to claim 44, wherein each of said plurality of cell-containing droplets includes cell suspensions identical to cell suspensions in the rest of said droplets, and wherein step b) is performed by providing the plurality of cell-containing droplets from one source.

47. The method according to claim 44, wherein each of said plurality of cell-containing droplets includes cell suspensions different to the cell suspensions in the rest of the cell-containing droplets, and wherein step b) is performed by dispensing the plurality of cell-containing droplets from a corresponding plurality of sources, each of said plurality of sources having a cell suspension different from the rest of the cell suspensions.

48. The method according to claim 44, wherein the cells include adherent cells, and wherein prior to step b), one or more of said plurality of locations are modified to produce a plurality of cell culture sites, and wherein adherent cells adhere to said plurality of cell culture sites.

49. The method according to claim 44, wherein the cells include adherent cells, and wherein said each location in step b) includes a cell culture site adapted for adhesion and proliferation of adherent cells, such that the adherent cells adhere to the cell culture site during steps c) to e).

50. The method according to claim 44, wherein the plurality of droplets containing cell culture medium are dispensed to the cell-containing droplets such that each droplet containing cell culture medium mixes with, or displaces and replaces, the respective cell-containing droplet.

51. The method according to claim 1, wherein steps b) to e) are conducted according to a cell culture protocol under control of a computer controller interfaced to said digital microfluidic device.

52. The method according to claim 1 further comprising performing one or more cell assays on the cell containing droplet after culturing the cells.

53. The method according to claim 52, wherein performing the one or more cell assays on the cell-containing droplet after culturing the cells includes detecting signals emitted from the cell containing droplet using a device capable of detecting a signal from a cell-containing droplet selected from the group consisting of optical sensors, optical detectors comprising a light source and a photodetector, optical detectors that measure any one or combination of absorbance, fluorescence, epifluorescence, and chemiluminescence, UV light detectors, radiometric detectors, any one of scanning, imaging, and confocal microscopy detectors, CCD cameras, and microplate readers.

54. The method according to claim 52 wherein at least a portion of the cells in the cell-containing droplet are alive when the one or more cell assays are performed.

55. The method according to claim 52, wherein performing one or more assays includes actuating electrodes of the array to dispense one or more assay reagents to the cell-containing droplet.

* * * * *

UNITED STATES PATENT AND TRADEMARK OFFICE
CERTIFICATE OF CORRECTION

PATENT NO. : 8,367,370 B2  
APPLICATION NO. : 12/285020  
DATED : February 5, 2013  
INVENTOR(S) : Wheeler et al.

Page 1 of 1

It is certified that error appears in the above-identified patent and that said Letters Patent is hereby corrected as shown below:

In the Claims:

Col. 21, line 54, 'e)' should be added between 'one' and 'are', such that claim 10 reads as follows:

10. The method according to claim 9, wherein steps d) and e) are performed one or more additional times.

Signed and Sealed this
Sixteenth Day of July, 2013

Teresa Stanek Rea
*Acting Director of the United States Patent and Trademark Office*